US009854790B2

(12) United States Patent
Ait-Ali et al.

(10) Patent No.: US 9,854,790 B2
(45) Date of Patent: Jan. 2, 2018

(54) DOMAIN 5 OF CD163 FOR USE IN ANTIVIRAL COMPOSITIONS AGAINST PRRS, AND TRANSGENIC ANIMALS

(71) Applicant: The University Court of the University of Edinburgh, Edinburgh (GB)

(72) Inventors: Tahar Ait-Ali, Lothian (GB); Simon Lillico, Lothian (GB); Alan Archibald, Lothian (GB); Christopher Bruce Alexander Whitelaw, Biggar (GB)

(73) Assignee: The University Court of the University of Edinburgh, Edinburgh (GB)

( * ) Notice: Subject to any disclaimer, the term of this patent is extended or adjusted under 35 U.S.C. 154(b) by 0 days.

(21) Appl. No.: 14/907,069

(22) PCT Filed: Jul. 24, 2014

(86) PCT No.: PCT/GB2014/052270
§ 371 (c)(1),
(2) Date: Jan. 22, 2016

(87) PCT Pub. No.: WO2015/011483
PCT Pub. Date: Jan. 29, 2015

(65) Prior Publication Data
US 2016/0165860 A1 Jun. 16, 2016

(30) Foreign Application Priority Data
Jul. 24, 2013 (GB) .................. 1313235.2

(51) Int. Cl.
*A01K 67/027* (2006.01)
*C07K 14/705* (2006.01)
*C12N 15/85* (2006.01)
*A61K 38/00* (2006.01)

(52) U.S. Cl.
CPC .... *A01K 67/0275* (2013.01); *C07K 14/70596* (2013.01); *C12N 15/8509* (2013.01); *A01K 2217/072* (2013.01); *A01K 2217/077* (2013.01); *A01K 2227/108* (2013.01); *A01K 2267/02* (2013.01); *A61K 38/00* (2013.01); *C07K 2319/02* (2013.01); *C07K 2319/30* (2013.01); *C12N 2800/30* (2013.01); *C12N 2800/80* (2013.01)

(58) Field of Classification Search
None
See application file for complete search history.

(56) References Cited

U.S. PATENT DOCUMENTS

| 5,168,062 A | 12/1992 | Stinski |
| 9,090,913 B2 | 7/2015 | Kong et al. |
| 2005/0271685 A1 | 12/2005 | Calvert et al. |

FOREIGN PATENT DOCUMENTS

| CN | 102851279 A | 1/2013 |
| WO | WO-00/67796 A1 | 11/2000 |
| WO | WO-2012/158828 A1 | 11/2012 |

OTHER PUBLICATIONS

Yu et al. Cell Res 2011;21:1638-40.*
Wells et al. J Virol 2017; 91/2:e01521-16, pp. 1-11.*
Aigner et al., Transgenic pigs for xenotransplantation: selection of promoter sequences for reliable transgene expression, Curr. Opin. Organ Transplant., 15(2):201-6 (2010).
Ben-Bassat et al., Processing of the initiation methionine from proteins: properties of the *Escherichia coli* methionine aminopeptidase and its gene structure, J. Bacteriol., 169(2):751-7 (1987).
Berman et al., Detection of antibodies to herpes simplex virus with a continuous cell line expressing cloned glycoprotein D, Science, 222(4623):524-7 (1983).
Brinster et al., Regulation of metallothionein—thymidine kinase fusion plasmids injected into mouse eggs, Nature, 296(5852):39-42 (1982).
Cong et al., Multiplex genome engineering using CRISPR/Cas systems, Science, 339(6121):819-23 (2013).
Das et al., The minor envelope glycoproteins GP2a and GP4 of porcine reproductive and respiratory syndrome virus interact with the receptor CD163, J. Virol., 84(4):1731-40 (2010).
George et al., An analysis of protein domain linkers: their classification and role in protein folding, Protein Eng., 15(11):871-9 (2002).
Gorman et al., The Rous sarcoma virus long terminal repeat is a strong promoter when introduced into a variety of eukaryotic cells by DNA-mediated transfection, Proc. Natl. Acad. Sci. USA, 79(22):6777-81 (1982).
Hochuli et al., Genetic approach to facilitate purification of recombinant proteins with a novel metal chelate adsorbent, Nature Biotechnology, 6:132-5 (1988).
International Preliminary Report on Patentability, International Application No. PCT/GB2014/052270, dated Jan. 26, 2016.
International Search Report and Written Opinion, International Application No. PCT/GB2014/052270, dated Oct. 24, 2014.
Jiang et al., Recombinant adenovirus expressing GP5 and M fusion proteins of porcine reproductive and respiratory syndrome virus induce both humoral and cell-mediated immune responses in mice, Vet. Immunol. Immunopathol., 113(1-2):169-80 (2006).
Kober et al., Optimized signal peptides for the development of high expressing CHO cell lines, Biotechnol. Bioeng., 110(4):1164-73 (2013).

(Continued)

*Primary Examiner* — Janice Li
(74) *Attorney, Agent, or Firm* — Marshall, Gerstein & Borun LLP

(57) ABSTRACT

The present invention relates to methods and compositions useful for the prevention and/or treatment of PRRS in animals, typically domestic pigs. The invention relates to proteins which comprise fragments of CD163, nucleic acid constructs encoding such proteins, and methods of modifying expression or activity of CD 163 in vivo.

10 Claims, 5 Drawing Sheets

(56) References Cited

OTHER PUBLICATIONS

Lee et al., Deletion of the cytoplasmic domain of CD163 enhances porcine reproductive and respiratory syndrome virus replication, Arch. Virol., 155(8):1319-23 (2010).
Mettenleiter et al., A glycoprotein gX-beta-galactosidase fusion gene as insertional marker for rapid identification of pseudorabies virus mutants, J. Virol. Methods, 30(1):55-65 (1990).
O'Regan et al., Cloning and nucleotide sequence of the phosphoenolpyruvate carboxylase-coding gene of Corynebacterium glutamicum ATCC13032, Gene, 77(2):237-51 (1989).
Ramirez et al., Engineered zinc finger nickases induce homology-directed repair with reduced mutagenic effects, Nucleic Acids Res., 40(12):5560-8 (2012).
Sahin-Toth et al., Cysteine scanning mutagenesis of the N-terminal 32 amino acid residues in the lactose permease of *Escherichia coli*, Protein Sci., 3(2):240-7 (1994).
Van Gorp et al., Identification of the CD163 protein domains involved in infection of the porcine reproductive and respiratory syndrome virus, J. Virol., 84(6):3101-5 (2010).
Voellmy et al., Isolation and functional analysis of a human 70,000-dalton heat shock protein gene segment, Proc. Natl. Acad. Sci. USA, 82(15):4949-53 (1985).
von Heijne, Signal sequences. The limits of variation, J. Mol. Biol., 184(1):99-105 (1985).

\* cited by examiner

Pfuse-control   D14-Fc   D59-Fc

D55-Fc

Cycle threshold (Ct)

| Time post infection | D14 | D55 | D59 | pFUSE |
|---|---|---|---|---|
| 24 H | 26.06 | 30.03 | 25.24 | 25.69 |
| 48 H | 15.15 | 30.37 | 15.45 | 15.31 |
| 72 H | 15.46 | 29.59 | 14.80 | 14.18 |
| 120 H | no reading | 30.14 | 16.11 | 16.24 |

Fig 7

SEQUENCE LISTING

<160> NUMBER OF SEQ ID NOS: 15

<210> SEQ ID NO 1
<211> LENGTH: 1115
<212> TYPE: PRT
<213> ORGANISM: Sus scrofa

<400> SEQUENCE: 1

```
Met Asp Lys Leu Arg Met Val Leu His Glu Asn Ser Gly Ser Ala Asp
1               5                   10                  15

Phe Arg Arg Cys Ser Ala His Leu Ser Ser Phe Thr Phe Ala Val Val
                20                  25                  30

Ala Val Leu Ser Ala Cys Leu Val Thr Ser Ser Leu Gly Gly Lys Asp
            35                  40                  45

Lys Glu Leu Arg Leu Thr Gly Gly Glu Asn Lys Cys Ser Gly Arg Val
        50                  55                  60

Glu Val Lys Val Gln Glu Glu Trp Gly Thr Val Cys Asn Asn Gly Trp
65                  70                  75                  80

Asp Met Asp Val Val Ser Val Val Cys Arg Gln Leu Gly Cys Pro Thr
                85                  90                  95

Ala Ile Lys Ala Thr Gly Trp Ala Asn Phe Ser Ala Gly Ser Gly Arg
            100                 105                 110

Ile Trp Met Asp His Val Ser Cys Arg Gly Asn Glu Ser Ala Leu Trp
        115                 120                 125
```

-continued

```
Asp Cys Lys His Asp Gly Trp Gly Lys His Asn Cys Thr His Gln Gln
130                 135                 140

Asp Ala Gly Val Thr Cys Ser Asp Gly Ser Asp Leu Glu Met Arg Leu
145                 150                 155                 160

Val Asn Gly Gly Asn Arg Cys Leu Gly Arg Ile Glu Val Lys Phe Gln
                165                 170                 175

Gly Arg Trp Gly Thr Val Cys Asp Asp Asn Phe Asn Ile Asn His Ala
            180                 185                 190

Ser Val Val Cys Lys Gln Leu Glu Cys Gly Ser Ala Val Ser Phe Ser
        195                 200                 205

Gly Ser Ala Asn Phe Gly Glu Gly Ser Gly Pro Ile Trp Phe Asp Asp
210                 215                 220

Leu Val Cys Asn Gly Asn Glu Ser Ala Leu Trp Asn Cys Lys His Glu
225                 230                 235                 240

Gly Trp Gly Lys His Asn Cys Asp His Ala Glu Asp Ala Gly Val Ile
                245                 250                 255

Cys Leu Asn Gly Ala Asp Leu Lys Leu Arg Val Val Asp Gly Val Thr
            260                 265                 270

Glu Cys Ser Gly Arg Leu Glu Val Lys Phe Gln Gly Glu Trp Gly Thr
        275                 280                 285

Ile Cys Asp Asp Gly Trp Asp Ser Asp Ala Ala Val Ala Cys Lys
290                 295                 300

Gln Leu Gly Cys Pro Thr Ala Val Thr Ala Ile Gly Arg Val Asn Ala
305                 310                 315                 320

Ser Glu Gly Thr Gly His Ile Trp Leu Asp Ser Val Ser Cys His Gly
                325                 330                 335

His Glu Ser Ala Leu Trp Gln Cys Arg His His Glu Trp Gly Lys His
            340                 345                 350

Tyr Cys Asn His Asn Glu Asp Ala Gly Val Thr Cys Ser Asp Gly Ser
        355                 360                 365

Asp Leu Glu Leu Arg Leu Lys Gly Gly Ser His Cys Ala Gly Thr
370                 375                 380

Val Glu Val Glu Ile Gln Lys Leu Val Gly Lys Val Cys Asp Arg Ser
385                 390                 395                 400

Trp Gly Leu Lys Glu Ala Asp Val Val Cys Arg Gln Leu Gly Cys Gly
                405                 410                 415

Ser Ala Leu Lys Thr Ser Tyr Gln Val Tyr Ser Lys Thr Lys Ala Thr
            420                 425                 430

Asn Thr Trp Leu Phe Val Ser Ser Cys Asn Gly Asn Glu Thr Ser Leu
        435                 440                 445

Trp Asp Cys Lys Asn Trp Gln Trp Gly Gly Leu Ser Cys Asp His Tyr
450                 455                 460

Asp Glu Ala Lys Ile Thr Cys Ser Ala His Arg Lys Pro Arg Leu Val
465                 470                 475                 480

Gly Gly Asp Ile Pro Cys Ser Gly Arg Val Glu Val Gln His Gly Asp
                485                 490                 495

Thr Trp Gly Thr Val Cys Asp Ser Asp Phe Ser Leu Glu Ala Ala Ser
            500                 505                 510

Val Leu Cys Arg Glu Leu Gln Cys Gly Thr Val Val Ser Leu Leu Gly
        515                 520                 525

Gly Ala His Phe Gly Glu Gly Ser Gly Gln Ile Trp Ala Glu Glu Phe
530                 535                 540

Gln Cys Glu Gly His Glu Ser His Leu Ser Leu Cys Pro Val Ala Pro
```

-continued

```
            545                 550                 555                 560
        Arg Pro Asp Gly Thr Cys Ser His Ser Arg Asp Val Gly Val Cys
                        565                 570                 575
        Ser Arg Tyr Thr Gln Ile Arg Leu Val Asn Gly Lys Thr Pro Cys Glu
                        580                 585                 590
        Gly Arg Val Glu Leu Asn Ile Leu Gly Ser Trp Gly Ser Leu Cys Asn
                        595                 600                 605
        Ser His Trp Asp Met Glu Asp Ala His Val Leu Cys Gln Gln Leu Lys
                        610                 615                 620
        Cys Gly Val Ala Leu Ser Ile Pro Arg Gly Ala Pro Phe Gly Lys Gly
        625                 630                 635                 640
        Ser Glu Gln Val Trp Arg His Met Phe His Cys Thr Gly Thr Glu Lys
                        645                 650                 655
        His Met Gly Asp Cys Ser Val Thr Ala Leu Gly Ala Ser Leu Cys Ser
                        660                 665                 670
        Ser Gly Gln Val Ala Ser Val Ile Cys Ser Gly Asn Gln Ser Gln Thr
                        675                 680                 685
        Leu Ser Pro Cys Asn Ser Ser Ser Asp Pro Ser Ser Ser Ile Ile
                        690                 695                 700
        Ser Glu Glu Asn Gly Val Ala Cys Ile Gly Ser Gly Gln Leu Arg Leu
        705                 710                 715                 720
        Val Asp Gly Gly Arg Cys Ala Gly Arg Val Glu Val Tyr His Glu
                        725                 730                 735
        Gly Ser Trp Gly Thr Ile Cys Asp Asp Ser Trp Asp Leu Asn Asp Ala
                        740                 745                 750
        His Val Val Cys Lys Gln Leu Ser Cys Gly Trp Ala Ile Asn Ala Thr
                        755                 760                 765
        Gly Ser Ala His Phe Gly Glu Gly Thr Gly Pro Ile Trp Leu Asp Glu
                        770                 775                 780
        Ile Asn Cys Asn Gly Lys Glu Ser His Ile Trp Gln Cys His Ser His
        785                 790                 795                 800
        Gly Trp Gly Arg His Asn Cys Arg His Lys Glu Asp Ala Gly Val Ile
                        805                 810                 815
        Cys Ser Glu Phe Met Ser Leu Arg Leu Ile Ser Glu Asn Ser Arg Glu
                        820                 825                 830
        Thr Cys Ala Gly Arg Leu Glu Val Phe Tyr Asn Gly Ala Trp Gly Ser
                        835                 840                 845
        Val Gly Arg Asn Ser Met Ser Pro Ala Thr Val Gly Val Val Cys Arg
        850                 855                 860
        Gln Leu Gly Cys Ala Asp Arg Gly Asp Ile Ser Pro Ala Ser Ser Asp
        865                 870                 875                 880
        Lys Thr Val Ser Arg His Met Trp Val Asp Asn Val Gln Cys Pro Lys
                        885                 890                 895
        Gly Pro Asp Thr Leu Trp Gln Cys Pro Ser Ser Pro Trp Lys Lys Arg
                        900                 905                 910
        Leu Ala Ser Pro Ser Glu Glu Thr Trp Ile Thr Cys Ala Asn Lys Ile
                        915                 920                 925
        Arg Leu Gln Glu Gly Asn Thr Asn Cys Ser Gly Arg Val Glu Ile Trp
                        930                 935                 940
        Tyr Gly Gly Ser Trp Gly Thr Val Cys Asp Asp Ser Trp Asp Leu Glu
        945                 950                 955                 960
        Asp Ala Gln Val Val Cys Arg Gln Leu Gly Cys Gly Ser Ala Leu Glu
                        965                 970                 975
```

-continued

Ala Gly Lys Glu Ala Ala Phe Gly Gln Gly Thr Gly Pro Ile Trp Leu
        980                 985                 990

Asn Glu Val Lys Cys Lys Gly Asn Glu Thr Ser Leu Trp Asp Cys Pro
        995                 1000                1005

Ala Arg Ser Trp Gly His Ser Asp Cys Gly His Lys Glu Asp Ala
        1010                1015                1020

Ala Val Thr Cys Ser Glu Ile Ala Lys Ser Arg Glu Ser Leu His
        1025                1030                1035

Ala Thr Gly Arg Ser Ser Phe Val Ala Leu Ala Ile Phe Gly Val
        1040                1045                1050

Ile Leu Leu Ala Cys Leu Ile Ala Phe Leu Ile Trp Thr Gln Lys
        1055                1060                1065

Arg Arg Gln Arg Gln Arg Leu Ser Val Phe Ser Gly Gly Glu Asn
        1070                1075                1080

Ser Val His Gln Ile Gln Tyr Arg Glu Met Asn Ser Cys Leu Lys
        1085                1090                1095

Ala Asp Glu Thr Asp Met Leu Asn Pro Ser Gly Asp His Ser Glu
        1100                1105                1110

Val Gln
    1115

<210> SEQ ID NO 2
<211> LENGTH: 3399
<212> TYPE: DNA
<213> ORGANISM: Sus scrofa

<400> SEQUENCE: 2
atggtgctac ttgaagactc tggatctgca gactttagaa gatgttctgc ccatttaagt      60
tccttcactt tgctgtagt cgctgttctc agtgcctgct tggtcactag ttctcttgga     120
ggaaaagaca aggagctgag gctaacgggt ggtgaaaaca agtgctctgg aagagtggag     180
gtgaaagtgc aggaggagtg gggaactgtg tgtaataatg ctgggacat ggatgtggtc     240
tctgttgttt gtaggcagct gggatgtcca actgctatca aagccactgg atgggctaat     300
tttagtgcag gttctggacg catttggatg gatcatgttt cttgtcgagg gaatgagtca     360
gctctctggg actgcaaaca tgatggatgg ggaaagcata actgtactca ccaacaggat     420
gctggagtaa cctgctcaga tggatctgat ttagagatga ggctggtgaa tggaggaaac     480
cggtgcttag aagaataga agtcaaattt caagagcggt ggggaacagt gtgtgatgat     540
aacttcaaca taaatcatgc ttctgtggtt tgtaaacaac ttgaatgtgg aagtgctgtc     600
agtttctctg gttcagctaa ttttggagaa ggttctggac caatctggtt tgatgatctt     660
gtatgcaatg gaaatgagtc agctctctgg aactgcaaac atgaaggatg ggaaagcac     720
aattgcgatc atgctgagga tgctggagtg atttgcttaa atggagcaga cctgaaactg     780
agagtggtag atggactcac tgaatgttca ggaagattgg aagtgaaatt ccaaggagaa     840
tggggaacaa tctgtgatga tggctgggat agtgatgatg ccgctgtggc atgtaagcaa     900
ctgggatgtc caactgctgt cactgccatt ggtcgagtta acgccagtga ggaactggga     960
cacatttggc ttgacagtgt tcttgccat ggacacgagt ctgctctctg gcagtgtaga    1020
caccatgaat ggggaaagca ttattgcaat cataatgaag atgctggtgt gacatgttct    1080
gatggatcag atctggaact gagacttaaa ggtggaggca gccactgtgc tgggacagtg    1140
gaggtggaaa ttcagaaact ggtaggaaaa gtgtgtgata agaagctgggg actgaaagaa    1200

```
gctgatgtgg tttgcaggca gctgggatgt ggatctgcac tcaaaacatc atatcaagtt      1260
tattccaaaa ccaaggcaac aaacacatgg ctgtttgtaa gcagctgtaa tggaaatgaa      1320
acttctcttt gggactgcaa gaattggcag tggggtggac ttagttgtga tcactatgac      1380
gaagccaaaa ttacctgctc agcccacagg aaacccaggc tggttggagg ggacattccc      1440
tgctctggtc gtgttgaagt acaacatgga gacacgtggg gcaccgtctg tgattctgac      1500
ttctctctgg aggcggccag cgtgctgtgc agggaactac agtgcggcac tgtggtttcc      1560
ctcctggggg gagctcactt tggagaagga agtggacaga tctgggctga agaattccag      1620
gtgaggggca cgagtcccac ctttcactct gcccagtagc accccgccct gacgggacat      1680
gtagccacag cagggacgtc ggcgtagtct gctcaagata cacacaaatc cgcttggtga      1740
atggcaagac cccatgtgaa ggaagagtgg agctcaacat tcttgggtcc tgggggtccc      1800
tctgcaactc tcactgggac atggaagatg cccatgtttt atgccagcag cttaaatgtg      1860
gagttgccct ttctatcccg ggaggagcac cttttgggaa aggaagtgag caggtctgga      1920
ggcacatgtt tcactgcact gggactgaga agcacatggg agattgttcc gtcactgctc      1980
tgggcgcatc actctgttct tcagggcaag tggcctctgt aatctgctca gggaaccaga      2040
gtcagacact atccccgtgc aattcatcat cctcggaccc atcaagctct attatttcag      2100
aagaaagtgg tgttgcctgc atagggagtg gtcaacttcg cctggtcgat ggaggtggtc      2160
gttgtgctgg gagagtagag gtctatcctg ggcatcctg gggcaccatc tgtgatgaca      2220
gctgggacct gaatgatgcc catgtggtgt gcaaacagct gagctgtgga tgggccatta      2280
atgccactgt ttctgctcat tttggggaag aacagggcc catttggctg gatgagataa      2340
actgtaatgg aaaagaatct catatttggc aatgccactc acatggttgg gggcggcaca      2400
attgcaggca taaggaggat gcaggagtca tctgctcaga gttcatgtct ctgagactga      2460
tcagtgaaaa cagcagagag acctgtgcag ggcgcctgga agttttttac aacggagctt      2520
ggggcagcgt tggcaggaat agcatgtctc cagccacagt gggggtggta tgcaggcagc      2580
tgggctgtgc agacagaggg gacatcagcc ctgcatcttc agacaagaca gtgtccaggc      2640
acatgtgggt ggacaatgtt cagtgtccta aaggacctga cacactatgg cagtgccct      2700 catctccatg gaagaagaga ctggccagcc cctcagagga gacatggatc acatgtgcca      2760
acaaaataag acttcaagaa ggaaacacta attgttctgg acgtgtggag atctggtacg      2820
gaggttcctg gggcactgtg tgtgacgact cctgggacct tgaagatgct caggtggtgt      2880
gccgacagct gggctgtggc tcagcttttgg aggcaggaaa agagcccgca tttggccagg      2940
ggactgggcc catatggctc aatgaagtga agtgcaaggg gaatgaaccc tccttgtggg      3000
attgtcctgc cagatcctgg ggccacagtg actgtggaca caaggaggat gctgctgtga      3060
cgtgctcaga aattgcaaag agccgagaat ccctacatgc cacaggtcgc tcatcttttg      3120
ttgcacttgc aatctttggg gtcattctgt tggcctgtct catcgcattc ctcatttgga      3180
ctcagaagcg aagacagagg cagcggctct cagttttctc aggaggagag aattctgtcc      3240
atcaaattca ataccgggag atgaattctt gcctgaaagc agatgaaacg gatatgctaa      3300
atccctcagg agaccactct gaagtacaat gaaaaggaaa atgggaatta taacctggtg      3360
agttcagcct ttaagatacc ttgatgaaga cctggacta                            3399
```

<210> SEQ ID NO 3
<211> LENGTH: 101
<212> TYPE: PRT
<213> ORGANISM: Sus scrofa

```
<400> SEQUENCE: 3

Pro Arg Leu Val Gly Gly Asp Ile Pro Cys Ser Gly Arg Val Glu Val
1               5                   10                  15

Gln His Gly Asp Thr Trp Gly Thr Val Cys Asp Ser Asp Phe Ser Leu
            20                  25                  30

Glu Ala Ala Ser Val Leu Cys Arg Glu Leu Gln Cys Gly Thr Val Val
        35                  40                  45

Ser Leu Leu Gly Gly Ala His Phe Gly Glu Gly Ser Gly Gln Ile Trp
    50                  55                  60

Ala Glu Glu Phe Gln Cys Glu Gly His Glu Ser His Leu Ser Leu Cys
65              70                  75                  80

Pro Val Ala Pro Arg Pro Asp Gly Thr Cys Ser His Ser Arg Asp Val
                85                  90                  95

Gly Val Val Cys Ser
            100

<210> SEQ ID NO 4
<211> LENGTH: 51
<212> TYPE: DNA
<213> ORGANISM: Sus scrofa

<400> SEQUENCE: 4
tccctcaccg aaatgctatt ttcagcccac aggaaaccca ggctggttgg a         51

<210> SEQ ID NO 5
<211> LENGTH: 52
<212> TYPE: DNA
<213> ORGANISM: Sus scrofa

<400> SEQUENCE: 5
tcggcgtagt ctgctcaagt gagacccagg gaatgtgttc actttgttcc ca        52

<210> SEQ ID NO 6
<211> LENGTH: 20
<212> TYPE: DNA
<213> ORGANISM: Artificial Sequence
<220> FEATURE:
<223> OTHER INFORMATION: Primer for detecting editing events (forward)

<400> SEQUENCE: 6
aaaccaagag gcatgaatgg                                             20

<210> SEQ ID NO 7
<211> LENGTH: 20
<212> TYPE: DNA
<213> ORGANISM: Artificial Sequence
<220> FEATURE:
<223> OTHER INFORMATION: Primer to detect editing events (reverse)

<400> SEQUENCE: 7
tgtcccagtg agagttgcag                                             20

<210> SEQ ID NO 8
<211> LENGTH: 35
<212> TYPE: DNA
<213> ORGANISM: Artificial Sequence
<220> FEATURE:
<223> OTHER INFORMATION: D1-FW Primer

<400> SEQUENCE: 8
acgaattcca gaatggtgct acatgaaaac tctgg                            35
```

<210> SEQ ID NO 9
<211> LENGTH: 35
<212> TYPE: DNA
<213> ORGANISM: Artificial Sequence
<220> FEATURE:
<223> OTHER INFORMATION: D5-FW Primer

<400> SEQUENCE: 9
tcgatatcac acaggaaacc caggctggtt ggagg                       35

<210> SEQ ID NO 10
<211> LENGTH: 35
<212> TYPE: DNA
<213> ORGANISM: Artificial Sequence
<220> FEATURE:
<223> OTHER INFORMATION: D4-RV Primer

<400> SEQUENCE: 10
gccgatatcg ctgagcaggt aattttggct tcgtc                       35

<210> SEQ ID NO 11
<211> LENGTH: 35
<212> TYPE: DNA
<213> ORGANISM: Artificial Sequence
<220> FEATURE:
<223> OTHER INFORMATION: D5-RV Primer

<400> SEQUENCE: 11
taaccatggt gtatcttgag cagactacgc cgacg                       35

<210> SEQ ID NO 12
<211> LENGTH: 35
<212> TYPE: DNA
<213> ORGANISM: Artificial Sequence
<220> FEATURE:
<223> OTHER INFORMATION: D9-RV Primer

<400> SEQUENCE: 12
ccgatatcga gcacgtcaca gcagcatcct ccttg                       35

<210> SEQ ID NO 13
<211> LENGTH: 21
<212> TYPE: PRT
<213> ORGANISM: Artificial Sequence
<220> FEATURE:
<223> OTHER INFORMATION: Linker Peptide

<400> SEQUENCE: 13

Gly Ser Gly Ser Ser Arg Gly Gly Ser Gly Ser Gly Gly Ser Gly Gly
1               5                   10                  15

Gly Gly Ser Lys Leu
            20

<210> SEQ ID NO 14
<211> LENGTH: 1080
<212> TYPE: DNA
<213> ORGANISM: Artificial Sequence
<220> FEATURE:
<223> OTHER INFORMATION: IL2-D55-FC construct

<400> SEQUENCE: 14
atgtacagga tgcaactcct gtcttgcatt gcactaagtc ttgcacttgt cacgaattcg     60
atatccagga aacccaggct ggttggaggg gacattccct gctctggtcg tgttgaagta    120

-continued

```
caacatggag acacgtgggg caccgtctgt gattctgact tctctctgga ggcggccagc      180
gtgctgtgca gggaactaca gtgcggcact gtggtttccc tcctgggggg agctcacttt      240
ggagaaggaa gtggacagat ctgggctgaa gaattccagt gtgaggggca cgagtcccac      300
ctttcactct gcccagtagc accccgccct gacgggacat gtagccacag cagggacgtc      360
ggcgtagtct gctcaagata caccatggtt agatctccta catgccctac atgtcacaaa      420
tgcccagttc ctgaactctt gggtggacca tctgtcttca tcttcccgcc aaagcccaag      480
gacatcctct tgatctccca gaacgccaag gtcacgtgtg tggtggtgga tgtgagcgag      540
gaggagccgg acgtccagtt cagctggttt gtgaacaacg tagaagtaca cagctcag       600 acacaaccccc gtgaggagca gtacaacagc accttcagag tggtcagtgc cctccccatc    660
cagcaccagg actggatgag cggcaaggag ttcaaatgca aggtcaacaa caaagccctc     720
ccaagcccca tcgagaaaac catctcaaaa cccaaagggc tagtcagaaa accacaggta    780
tacgtcatgg gtccaccgac agagcagttg actgagcaaa cggtcagttt gacctgcttg    840
acctcaggct cctcccctaa cgacatcggt gtggagtgga ccagcaacgg catatagaa      900 aagaactaca gaacaccga gccagtgatg gactctgacg gttctttctt catgtacagc      960
aagctcaatg tggaaaggag caggtgggat agcagagcgc ccttcgtctg ctccgtggtc    1020
cacgagggtc tgcacaatca ccacgtggag aagagcatct cccggcctcc gggtaaatga    1080
```

<210> SEQ ID NO 15
<211> LENGTH: 1008
<212> TYPE: DNA
<213> ORGANISM: Artificial Sequence
<220> FEATURE:
<223> OTHER INFORMATION: D55-FC construct

<400> SEQUENCE: 15

```
cccaggctgg ttggagggga cattccctgc tctggtcgtg ttgaagtaca acatggagac       60
acgtggggca ccgtctgtga ttctgacttc tctctggagg cggccagcgt gctgtgcagg      120
gaactacagt gcggcactgt ggtttccctc ctggggggag ctcactttgg agaaggaagt      180
ggacagatct gggctgaaga attccagtgt gaggggcacg agtcccacct ttcactctgc      240
ccagtagcac cccgccctga cgggacatgt agccacagca gggacgtcgg cgtagtctgc      300
tcaagataca ccatggttag atctcctaca tgccctacat gtcacaaatg cccagttcct      360
gaactcttgg gtggaccatc tgtcttcatc ttcccgccaa agcccaagga catcctcttg      420
atctcccaga cgccaaggt cacgtgtgtg tggtggatg tgagcgagga ggagccggac       480
gtccagttca gctggtttgt gaacaacgta gaagtacaca cagctcagac aacccccgt      540 gaggagcagt acaacagcac cttcagagtg gtcagtgccc tccccatcca gcaccaggac      600
tggatgagcg gcaaggagtt caaatgcaag gtcaacaaca aagccctccc aagccccatc      660
gagaaaacca tctcaaaacc caaagggcta gtcagaaaac acaggtata cgtcatgggt      720 ccaccgacag agcagttgac tgagcaaacg gtcagtttga cctgcttgac ctcaggcttc      780
ctccctaacg acatcggtgt ggagtggacc agcaacgggc atatagaaaa gaactacaag      840
aacaccgagc cagtgatgga ctctgacggt tctttcttca tgtacagcaa gctcaatgtg      900
gaaaggagca ggtgggatag cagagcgccc ttcgtctgct ccgtggtcca cgagggtctg     960
cacaatcacc acgtggagaa gagcatctcc cggcctccgg gtaaatga                 1008
```

DOMAIN 5 OF CD163 FOR USE IN ANTIVIRAL COMPOSITIONS AGAINST PRRS, AND TRANSGENIC ANIMALS

The present invention relates to compositions and methods to prevent or treat porcine reproductive and respiratory syndrome virus (PRRSV) infection in animals. The invention also relates to animals which have been modified to provide resistance to infection by PRRSV.

INTRODUCTION

Porcine reproductive and respiratory syndrome virus (PRRSV) is a virus that causes a disease of pigs, called porcine reproductive and respiratory syndrome (PRRS).

This economically important, pandemic disease causes reproductive failure in breeding stock and respiratory tract illness in young pigs. Initially referred to as "mystery swine disease" and "mystery reproductive syndrome," it was first reported in 1987 in North America and Central Europe. It is estimated that the disease costs the United States swine industry around $600 million annually.

PRRSV enters alveolar macrophages via a set of macrophage cell surface markers: CD169 and CD163. The role of CD169 sialoadhesin was discovered by the group of Hans Nauwynck in Ghent. The role of CD163 was discovered by scientists working with Pfizer (Calvert et al. 2007). Calvert et al (2007) demonstrated that transfection of any non-susceptible cells with CD163 can turn the cells susceptible to PRRSV. That has allowed for the generation of vaccine strains without the need of using Marc-145 cells.

Van Gorp et al. (J Virol. 2010 March; 84(6):3101-5. Identification of the CD163 protein domains involved in infection of the porcine reproductive and respiratory syndrome virus. Van Gorp H et al.) have demonstrated that the domains 5 to 9 are important for the PRRSV entry into non-susceptible cells. She has highlighted that domain 5 may be critical.

Das et al. ("The Minor Envelope Glycoproteins GP2a and GP4 of Porcine Reproductive and Respiratory Syndrome Virus Interact with the Receptor CD163", JOURNAL OF VIROLOGY, February 2010, p. 1731-1740) have demonstrated that that the PRRSV glycoprotein GP2A and GP4 interact physically with CD163.

US 20050271685 held by Pfizer (Zoetis) suggests that the use of CD163 molecule can make cells susceptible to PRRSV and ASFV.

WO 2012158828 describes PRRS resistant animals in which the SIGLEC1 and/or CD163 genes have been inactivated. However, CD163, has roles in normal physiological activities. It is therefore undesirable to inactive this gene as it may have undesirable and unforeseeable knock-on effects on the animal.

There remains a need for improvements in the prevention and treatment of PRRSV.

STATEMENTS OF THE INVENTION

According to a first aspect of the invention, there is provided an isolated or synthetic protein comprising CD163, or a biologically active fragment or variant thereof, for the prevention or treatment of PRRSV in an animal.

Preferably the animal is a porcine animal, more preferably a pig (Sus scrofa), and most preferably a domestic pig (Sus scrofa domesticus or Sus domesticus).

Suitably the protein comprises one or more extracellular domains of CD163, but excludes transmembrane domains and/or intracellular domains.

Preferably the isolated or synthetic protein comprises a fragment of CD163, wherein said fragment comprises domain 5 of CD163, or a biologically active fragment or variant thereof.

It is believed that domain 5 is the critical portion of CD163 that mediates PRRSV infection into cells. Accordingly, provision of a protein comprising domain 5 (or a functional equivalent) provides a protein which can bind to PRRSV or otherwise interfere with the infection process, and thus prevent infection of cells.

It has surprisingly been found that fragments of CD163, rather than the complete protein, are more effective as decoys to prevent PRRSV infection.

Suitably the protein comprises a fragment of CD163, wherein said fragment consists of at least a portion of domains 5 to 9 of CD163, or a biologically active fragment or variant thereof. Preferably said protein comprises domain 5, or a biologically active fragment or variant thereof.

In some embodiments the protein comprises domain 5, or a biologically active fragment or variant thereof, and not more than three of domains 6, 7, 8 or 9, or fragments or variants thereof. For example, the protein can comprise domain 5, or a biologically active fragment or variant thereof, and one of the following:
- domains 6, 7 and 8, or fragments or variants thereof;
- domains 6, 7 and 9, or fragments or variants thereof;
- domains 6, 8 and 9, or fragments or variants thereof; or
- domains 7, 8 and 9, or fragments or variants thereof.

Preferably the protein comprises domain 5 and not more than two of domains 6, 7, 8 or 9, or fragments or variants thereof, and more preferably not more than one of domains 6, 7, 8 or 9, or a fragment or variant thereof.

In a particularly preferred embodiment the fragment consists of domain 5 alone, or a biologically active fragment or variant thereof. It has been found that fragments of CD163 which consist of domain 5 without additional domains (e.g. 1, 2, 3, 4, 6, 7, 8 or 9) are especially effective when used as decoys to prevent PRRS infection of susceptible cells.

Domain 5 of CD163 has the amino acid sequence:

```
                                             (SEQ ID NO 3)
PRLVGGDIPCSGRVEVQHGDTWGTVCDSDFSLEAASVLCRELQCGTV

VSLLGGAHFGEGSGQIWAEEFQCEGHESHLSLCPVAPRPDGTCSHSR

DVGVVCS
```

For the avoidance of doubt, it is emphasised that the present invention include variants of this sequence or fragments thereof which retain the ability to bind to PRRSV and/or otherwise prevent or inhibit PRRSV infection, and as such are 'biologically active'. Details of various types of variants are described below, but include deletions, additions, substitutions, amino acid modifications and the like, provided that they do not prevent binding of the protein to PRRSV and/or otherwise eliminate its ability to prevent or inhibit PRRSV infection.

The present invention includes biologically-active proteins comprising an amino acid sequences which is at least 75%, 80%, 85%, 90%, 95% or 99% identical to SEQ ID NO 3.

"% identity" defines the relation between two or more polypeptides on the basis of a comparison between their aligned sequences.

Identity can be calculated by known methods. Identity, or homology, percentages as mentioned herein are those that can be calculated with the GAP program, running under GCG (Genetics Computer Group Inc., Madison, Wis., USA). Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Nat. Acad Sci. USA 85:2444, 1988; Higgins & Sharp, Gene, 73:23744, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, Md. 20894, US) and on the Internet, for use in connection with the sequence analysis programs blastp, blastn, blastx, tblastn and tblastx. Additional information can be found at the NCBI web site.

Parameters for polypeptide sequence comparison included the following:

Algorithm: Needleman and Wunsch, J. Mol. Biol. 1970, 48: 443-453.

As a comparison matrix for amino acid alignments the Blosum62 matrix is used (Henikoff and Henikoff, supra) using the following parameters:

Gap penalty: 8
Gap length penalty: 2
No penalty for end gaps.

The present invention thus, in certain embodiments, provides the protein described above, which is suitable for use in the prevention (e.g. prophylaxis) or treatment of PRRS in pigs.

Accordingly, the present invention provides an isolated or synthetic protein comprising the sequence:

```
                                        (SEQ ID NO 3)
PRLVGGDIPCSGRVEVQHGDTWGTVCDSDFSLEAASVLCRELQCGTV

VSLLGGAHFGEGSGQIWAEEFQCEGHESHLSLCPVAPRPDGTCSHSR

DVGVVCS
``` or a biologically active fragment or variant thereof for the prevention or treatment of PRRS in an animal.

Preferably said isolated synthetic protein does not contain the complete sequences of each of domains 6 to 9, whether said sequence are contiguous or non-contiguous. In other words, preferably the protein does not contain all of domains 5 to 9 CD163 in their entirety, but rather has at least a portion, and in some cases all, of domains 6 to 9 removed.

It will be apparent to the skilled person that the entire polypeptide of domain 5/SEQ ID NO 3 may not be required to bind to CD163, and thus fragments representing a portion of domain 5 may be suitable for the present invention.

Suitably the protein of the present invention is a fusion protein.

In one embodiment the protein is a fusion of CD163 or a biologically active fragment or variant thereof and an immunoglobulin (antibody) Fc fragment. Addition of an immunoglobulin Fc fragment can add stability and deliverability to proteins of the present invention. The Fc fragment can be a complete Fc region or a portion thereof. For example, the Fc fragment can be the Fc region of an IgG, such as IgG2bFc.

The protein of the present invention suitably comprises the addition of a signal peptide, e.g. a secretory peptide which promotes secretion of the protein from the cell in which translation occurs. Suitable secretory peptides are well-known in the art, and include the IL2 secretory domain.

Various signal peptides, and means for their optimization are set out in Kober L, Zehe C, Bode J (April 2013), "Optimized signal peptides for the development of high expressing CHO cell lines". Biotechnol. Bioeng. 110 (4): 1164-73, and von Heijne G (July 1985). "Signal sequences: The limits of variation". J Mol Biol 184 (1): 99-105. Such signal peptides can be used in the present invention.

Preferably the signal peptide is suitable to direct secretion from the cell type or species of animal in which translation occurs.

The fusion protein can comprise a peptide to allow identification and/or purification of the protein. For example, the fusion protein can comprise a GST protein, FLAG peptide, or a hexa-his peptide (6×His-tag) which can be isolated using affinity chromatography with nickel or cobalt resins.

A fusion protein according to the present invention may comprise one or more linker peptides. A suitable linker peptide has the sequence GSGSSRGGSGSGGSGGGGSKL (SEQ ID NO 13), but many other sequences would be suitable. Suitable linkers are well known in the art, and are typically rich in glycine for flexibility, and may comprise serine and/or threonine for solubility. Further information can be found, inter alia, at George R A and Heringa J. 'An analysis of protein domain linkers: their classification and role in protein folding'. Protein Eng, 2002 November; 15(11) 871-9.

In one embodiment of the invention the protein comprises a fusion of an IL2 signal peptide, domain 5 of CD163 (or a biologically active fragment or variant thereof) and the Fc fragment of an immunoglobulin. Suitably the Fc fragment is the Fc fragment of IgG. For example if can be the fragment IgG2bFc, e.g. rat IgG2bFc.

Suitably the protein is the fusion protein described as D55, D55-FC, or IL2-D55-FC below.

According to a second aspect of the invention there is provided a method of treating or preventing an infection in an animal comprising administration to said animal a composition comprising an isolated or synthetic protein comprising CD163 or a biologically active fragment or variant thereof.

Such a synthetic protein can act as a decoy for the PRRS virus. The decoy binds to the virus and therefore the virus does not bind to membrane bound CD163 and thus infect cells.

Accordingly, it is preferred that the synthetic CD163 protein is adapted to be soluble in plasma.

By providing a fusion protein of CD163 and Fc, for example, solubility and stability in vivo can be improved.

The composition can be administered via any suitable route. Such routes include, but are not limited to, oral and parenteral routes, such as intravenous (iv), intraperitoneal (ip), rectal, topical, ophthalmic, nasal, and transdermal.

The invention provides formulations comprising an active of the disclosure formulated for pharmaceutical use and optionally further comprising a pharmaceutically acceptable diluent, excipient and/or carrier.

The invention therefore includes pharmaceutical formulations which may include, in addition to active ingredient, a pharmaceutically acceptable diluent, excipient and/or carrier. Such formulations may be used in the methods of the disclosure. Additionally or alternatively, pharmaceutical formulations may include a buffer, stabiliser and/or other material well known to those skilled in the art. Such materials should be non-toxic and should not interfere with the efficacy of the active ingredient. The precise nature of the carrier or other material will depend on the route of administration, which may be any suitable route, for example by a parenteral route and particularly by infusion or injection (with or without a needle). The route of administration may be subcutaneous injection. The route of administration may be intravenous injection or infusion. Other routes of administration which may be used include administration by inhalation or intranasal administration.

Compositions are provided that include one or more of the actives that are disclosed herein in a carrier. The compositions can be prepared in unit dosage form for administration to a subject. The amount and timing of administration are at the discretion of the treating physician to achieve the desired purposes. The active may be formulated for systemic or local administration. In one example, the active formulated for parenteral administration, such as subcutaneous or intravenous administration.

Actual methods for preparing administrable compositions, whether for intravenous or subcutaneous administration or otherwise, will be known or apparent to those skilled in the art and are described in more detail in such publications as Remington's Pharmaceutical Science, 19th ed., Mack Publishing Company, Easton, Pa. (1995).

In embodiments of the present invention the administration of the composition may comprise delivering an expression vector to a subject, the vector being adapted for expression in the subject, and thereby causing the composition to be synthesized by the subject.

Various suitable expression vectors are described below.

According to a third aspect of the invention there is provided an isolated or synthetic nucleic acid construct which encodes the above-mentioned isolated or synthetic protein comprising CD163 or a biologically active fragment or variant thereof.

Said isolated or synthetic nucleic acid suitably comprises at least one expression control sequence operably linked to said nucleotide sequence encoding CD163, or a biologically active fragment or variant thereof, to drive expression of CD163, or a biologically active fragment or variant thereof. Such expression control sequences generally comprise a promoter sequence and additional sequences which regulate transcription and translation and/or enhance expression levels. Suitable expression control sequences are well known in the art and include eukaryotic, prokaryotic, or viral promoter or poly-A signal. Expression control and other sequences will, of course, vary depending on the host cell selected or can be made inducible. Examples of useful promoters are the SV-40 promoter (Science 1983, 222: 524-527), the metallothionein promoter (Nature 1982, 296: 39-42), the heat shock promoter (Voellmy et al., P.N.A.S. USA 1985, 82: 4949-4953), the PRV gX promoter (Mettenleiter and Rauh, J. Virol. Methods 1990, 30: 55-66), the human CMV IE promoter (U.S. Pat. No. 5,168,062), the Rous Sarcoma virus LTR promoter (Gorman et al., P.N.A.S. USA 1982, 79: 6777-6781), or human elongation factor 1 alpha or ubiquitin promoter. Suitable control sequences to drive expression in animals, e.g. pigs, are well known in the art. The expression control sequences can drive ubiquitous expression or tissue- or cell-specific expression. The expression control sequence can be, for example, a viral or porcine promoter. A suitable promoter can be ubiquitous (e.g. the CAG promoter) tissue restricted (e.g. the CMV immediate early promoter which is known to be expressed predominantly in exocrine cells) or tissue specific (e.g. CSF1 receptor promoter which is specific to cells of the mononuclear macrophage lineage, or a synthetic liver specific promoter). Further exemplary promoters for porcine expression can be found in, for example, Aigner et al., 'Transgenic pigs for xenotransplantation: selection of promoter sequences for reliable transgene expression'. Curr Opin Organ Transplant. 2010 April; 15(2): 201-6. Many other suitable control sequences are known in the art, and it would be routine for the skilled person to select suitable sequences for the expression system being used.

Suitably the nucleic acid construct comprises a sequence encoding fusion protein IL2-D55-Fc (D55 encoding region in lower case), such as:

(SEQ ID NO 14)
ATGTACAGGATGCAACTCCTGTCTTGCATTGCACTAAGTCTTGCACT

TGTCACGAATTCGATATCcaggaaacccaggctggttggaggggaca ttccctgctctggtcgtgttgaagtacaacatggagacacgtggggc accgtctgtgattctgacttctctctggaggcggccagcgtgctgtg cagggaactacagtgcggcactgtggtttccctcctgggggagctc actttggagaaggaagtggacagatctgggctgaagaattccagtgt gaggggcacgagtcccacctttcactctgcccagtagcaccccgccc tgacgggacatgtagccacagcagggacgtcggcgtagtctgctcaa gatacacCATGGTTAGATCTCCTACATGCCCTACATGTCACAAATGC

CCAGTTCCTGAACTCTTGGGTGGACCATCTGTCTTCATCTTCCCGCC

AAAGCCCAAGGACATCCTCTTGATCTCCCAGAACGCCAAGGTCACGT

GTGTGGTGGTGGATGTGAGCGAGGAGGAGCCGGACGTCCAGTTCAGC

TGGTTTGTGAACAACGTAGAAGTACACACAGCTCAGACACAACCCCG

TGAGGAGCAGTACAACAGCACCTTCAGAGTGGTCAGTGCCCTCCCCA

TCCAGCACCAGGACTGGATGAGCGGCAAGGAGTTCAAATGCAAGGTC

AACAACAAAGCCCTCCCAAGCCCCATCGAGAAAACCATCTCAAAACC

CAAAGGGCTAGTCAGAAAACCACAGGTATACGTCATGGGTCCACCGA

CAGAGCAGTTGACTGAGCAAACGGTCAGTTTGACCTGCTTGACCTCA

GGCTTCCTCCCTAACGACATCGGTGTGGAGTGGACCAGCAACGGGCA

TATAGAAAAGAACTACAAGAACACCGAGCCAGTGATGGACTCTGACG

GTTCTTTCTTCATGTACAGCAAGCTCAATGTGGAAAGGAGCAGGTGG

GATAGCAGAGCGCCCTTCGTCTGCTCCGTGGTCCACGAGGGTCTGCA

CAATCACCACGTGGAGAAGAGCATCTCCCGGCCTCCGGGTAAATGA

Suitably the nucleic acid construct comprises a sequence encoding construct D55-Fc (D55 encoding region in lower case), such as:

(SEQ ID NO 15)
cccaggctggttggaggggacattccctgctctggtcgtgttgaagt acaacatggagacacgtggggcaccgtctgtgattctgacttctctc

```
tggaggcggccagcgtgctgtgcagggaactacagtgcggcactgtg gtttccctcctgggggagctcactttggagaaggaagtggacagat ctgggctgaagaattccagtgtgaggggcacgagtcccacctttcac tctgcccagtagcaccccgccctgacgggacatgtagccacagcagg gacgtcggcgtagtctgctcaagatacacCATGGTTAGATCTCCTAC

ATGCCCTACATGTCACAAATGCCCAGTTCCTGAACTCTTGGGTGGAC

CATCTGTCTTCATCTTCCCGCCAAAGCCCAAGGACATCCTCTTGATC

TCCCAGAACGCCAAGGTCACGTGTGTGGTGGTGGATGTGAGCGAGGA

GGAGCCGGACGTCCAGTTCAGCTGGTTTGTGAACAACGTAGAAGTAC

ACACAGCTCAGACACAACCCCGTGAGGAGCAGTACAACAGCACCTTC

AGAGTGGTCAGTGCCCTCCCCATCCAGCACCAGGACTGGATGAGCGG

CAAGGAGTTCAAATGCAAGGTCAACAACAAAGCCCTCCCAAGCCCCA

TCGAGAAAACCATCTCAAAACCCAAAGGGCTAGTCAGAAAACCACAG

GTATACGTCATGGGTCCACCGACAGAGCAGTTGACTGAGCAAACGGT

CAGTTTGACCTGCTTGACCTCAGGCTTCCTCCCTAACGACATCGGTG

TGGAGTGGACCAGCAACGGGCATATAGAAAAGAACTACAAGAACACC

GAGCCAGTGATGGACTCTGACGGTTCTTTCTTCATGTACAGCAAGCT

CAATGTGGAAAGGAGCAGGTGGGATAGCAGAGCGCCCTTCGTCTGCT

CCGTGGTCCACGAGGGTCTGCACAATCACCACGTGGAGAAGAGCATC

TCCCGGCCTCCGGGTAAATGA
```

D55-Fc lacks the secretory signal peptide.

Due to the degeneracy of the genetic code, polynucleotides encoding an identical or substantially identical amino acid sequence may utilise different specific codons (e.g. synonymous base substitutions). All polynucleotides encoding the proteins as defined above are considered to be part of the invention.

According to a fourth aspect of the present invention there is provided an expression vector, said vector comprising a nucleotide sequence encoding CD163, or a biologically active fragment or variant thereof.

Such vectors suitably comprise an isolated or synthetic nucleic acid construct as described above.

The vectors according to the invention are suitable for transforming a host cell. Examples of suitable cloning vectors are plasmid vectors such as pBR322, the various pUC, pEMBL and Bluescript plasmids, or viral vectors such as HVT (Herpes Virus of Turkeys), MDV (Marek Disease Virus), ILT (Infectious Laryngotracheitis Virus), FAV (Fowl Adenovirus), FPV (FowlpoxVirus), or NDV (Newcastle Disease Virus). pcDNA3.1 is a particularly preferred vector for expression in animal cells.

After the polynucleotide has been cloned into an appropriate vector, the construct may be transferred into the cell, bacteria, or yeast by means of an appropriate method, such as electroporation, CaCl$_2$ transfection or lipofectins. When a baculovirus expression system is used, the transfer vector containing the polynucleotide may be transfected together with a complete baculo genome.

These techniques are well known in the art and the manufacturers of molecular biological materials (such as Clontech, Stratagene, Promega, and/or Invitrogen) provide suitable reagents and instructions on how to use them.

Furthermore, there are a number of standard reference text books providing further information on this, e.g. Rodriguez, R. L. and D. T. Denhardt, ed., "Vectors: A survey of molecular cloning vectors and their uses", Butterworths, 1988; Current protocols in Molecular Biology, eds.: F. M. Ausubel et al., Wiley N.Y., 1995; Molecular Cloning: a laboratory manual, supra; and DNA Cloning, Vol. 1-4, 2nd edition 1995, eds.: Glover and Hames, Oxford University Press).

Details of preferred proteins according to the present invention for expression via the vector are described above.

The vector may be adapted to provide transient expression in a host cell or stable expression. Stable expression can be achieved, for example, through integration of the nucleotide sequence encoding CD163 or a biologically active fragment or variant thereof into the genome of the host cell.

Suitable viral vectors include retroviral vectors (including lentiviral vectors), adenoviral vectors, adeno-associated viral (AAV) vectors, and alphaviral vectors.

The vector of the present invention can be present in a virion.

Vectors according to the present invention can be used in transforming cells for expression of a protein according to the present invention. This can be done in cell culture to produce recombinant protein for harvesting, or it can be done in vivo to deliver a protein according to the present invention to an animal.

In a fifth aspect the present invention provides a cell population in which cells comprise a synthetic genetic construct adapted express a protein according to the present invention.

Preferably said cell population is present in a cell-culture system in a suitable medium to support cell growth.

The cells can be eukaryotic or prokaryotic.

Polynucleotides of the present invention may be cloned into any appropriate expression system. Suitable expression systems include bacterial expression system (e.g. *Escherichia coli* DH5α), a viral expression system (e.g. Baculovirus), a yeast system (e.g. *Saccharomyces cerevisiae*) or eukaryotic cells (e.g. COS-7, CHO, BHK, HeLa, HD11, DT40, CEF, or HEK-293T cells). A wide range of suitable expression systems are available commercially. Typically the polynucleotide is cloned into an appropriate vector under control of a suitable constitutive or inducible promoter and then introduced into the host cell for expression.

Suitably the cells are animal cells, more preferably they are mammalian cells, and most preferably pig cells.

Suitably said synthetic genetic construct is adapted to express a secretory variant of CD163.

Suitably such cells comprise a vector as set out above.

Preferably the cells are adapted such that expression of the protein according to the present invention is inducible.

In a sixth aspect the present invention provides a genetically edited non-human animal comprising a genetic modification which alters the expression or activity of CD163.

Preferably the animal is a porcine animal, more preferably a pig (Sus scrofa), and most preferably a domestic pig (Sus scrofa domesticus or Sus domesticus).

In a first embodiment, at least a portion of the CD163 gene has been altered to abrogate its ability to bind to PRRSV.

Preferably the region of the gene encoding domain 5 of CD163 has been altered. More preferably alterations to the CD163 gene are only present in the region encoding domain 5 (exon 7) or flanking non-coding regions.

CD163 is a protein with a role in normal cellular functions. Thus, completely knocking out the function of GD163 is undesirable as it will have knock on effects on the animal.

Accordingly, the present invention provides a solution to this by targeting modifications to domain 5 of CD163. Such modifications can thus prevent PRRSV from infecting cells, because it cannot bind to domain 5, but does not completely abrogate its normal cellular functions, which are not restricted to domain 5.

In a second embodiment the animal is modified to contain a synthetic genetic construct adapted to express a protein according to the present invention.

Suitably the CD163 is a secretory form, i.e. it is not membrane-bound.

Suitably biologically-active variants of CD163 (including fragments focussed on domain 5) are discussed above in more detail.

Animals comprising such a modification will express a decoy form of CD163 which will bind to PRRSV, and/or otherwise prevent or inhibit PRSSV infection, and thus prevent PRRS or reduce its severity.

Editing of the CD163 gene sequence can suitably be achieved by any one or more of:
  Deleting at least a portion of the CD163 gene;
  Inserting a sequence into the CD163 gene; and
  Replacing at least a portion of the CD163 gene. Such a replacement is termed an 'introgression' or substitution.

Genetically edited animals according to the present invention preferably demonstrate one or more of the following phenotypes:
  an altered, especially increased, disease resilience or tolerance;
  an altered immune response; and
  an altered stress response.

More particularly, beneficial effects of the genetic modification may include improved tolerance or resistance to:
  Virus infection, e.g. PRRS infection in pigs.
  Pathogen infection, other than viral infection; and
  General or specific stressors.

In a particularly preferred aspect of the present invention the genetically edited animal is a pig which has improved tolerance to PRRS infection.

An animal can be said to be more tolerant to infection when the mortality rate, morbidity rate, the proportion of animals showing significant morbidity (e.g. weight loss or decreased growth rate), the level of morbidity or the duration of morbidity is reduced. Any statistically significant reduction (e.g. 95% confidence, or 99% confidence using an appropriate test) in the mortality or morbidity between a population of genetically edited pigs and a population of equivalent non-edited pigs when exposed to PRRS of the same virulence level (ideally the same isolate) demonstrates improved tolerance.

According to a seventh aspect the invention provides a method of producing a genetically edited non-human animal comprising the steps of:
  Providing a non-human animal cell;
  Editing the genetic content of the cell to create a modification which alters the expression or activity of CD163 or a biologically active fragment or variant thereof as set out above; and
  Generating an animal from said cell.

Preferably the animal is a porcine animal, more preferably a pig (Sus scrofa), and most preferably a domestic pig (Sus scrofa domesticus or Sus domesticus).

Suitably the modification alters the region of the CD163 gene which codes for domain 5 of CD163, i.e. exon 7, or flanking intronic regions.

Alternatively the modification introduces a sequence which encodes CD163 or a biologically active fragment or variant thereof as set out above which is able to act as a decoy.

The editing step suitably comprises:
  Introducing a site specific nuclease to the cell, the nuclease being adapted to bind to a suitable target sequence in the CD163 gene;
  Incubating said cell under suitable conditions for said nuclease to act upon the DNA at or near to said target sequence; and
  Thereby induce recombination, homology-directed repair (HDR) or non-homologous end joining (NHEJ) at or near the target site.

The non-human animal cell can be a somatic cell, a gamete, a germ cell, a gametocyte, a stem cell (e.g. a totipotent stem cell or pluripotent stem cell) or a zygote.

The method can optionally involve cloning, e.g. somatic cell nuclear transfer (SCNT). In such an embodiment the genetic editing event is carried out on a somatic cell, after which the edited nucleus is transferred to an enucleated egg cell. Typically a population of somatic cells will be edited and cells in which a desired editing event has occurred will be used to provide donor nuclei for SCNT. Processes for SCNT have been well described in the art and would be known to the skilled person.

However, it is an advantage of the present invention that editing can be performed without the need for cloning.

Preferably the method is performed on a zygote. The term 'zygote' can be used in a strict sense to refer to the single cell formed by the fusion of gametes. However, it can also be used more broadly in the present context to refer to the cell bundle resulting from the first few divisions of the true zygote—this is more properly known as the morula.

It is preferred that the present method is at least initiated, and preferably completed, in the zygote at the single cell stage. This should result in all cells of the animal containing the same edit. It is, however, possible that the zygote may divide while the editing process is occurring. Depending on when the cell division occurs relative to the stage of the editing process, it is possible that one of the following will occur:
  All cells will contain the same edit because they are derived from the a single cell which was edited before division occurred;
  All cells will contain the same edit because identical editing events occurred in the daughter cells after division occurred;
  A mosaic of cells with and without editing events is created because the cell divided before the editing event occurs and only one daughter cell was edited; and
  A mosaic of cells with different edits is created because the cell divided and differing editing events happened in the daughter cells.

Editing can also be conducted at after the first cell division, and the results may be of interest. However, this is generally not preferred where the desired result is a non-mosaic animal.

Accordingly, in a preferred embodiment the method comprises the steps of:
  Providing a zygote of the non-human animal;
  Introducing a site specific nuclease to the zygote which is adapted to bind to a suitable target sequence in the CD163 gene;
  Incubating said zygote under suitable conditions for said nuclease to act upon the DNA at or near to said target sequence; and Generating an animal from said genetically edited zygote.

It should be noted that the site specific nuclease can be introduced to a cell in any suitable form. For example, the nuclease can be provided directly into the cell as a functional protein. Alternatively, the nuclease can be provided into the cell in the form of a precursor or template from which the active nuclease is produced by the cell. In a preferred embodiment an mRNA encoding the nuclease is introduced into the cell, e.g. by injection. The mRNA is then expressed by the cell to form the functioning protein. Using mRNA in this way allows rapid but transient expression of the nuclease within the cell, which is ideal for the purposes of genetic editing.

It should also be noted that the term 'nuclease' is intended to cover any biological enzyme which creates a single or double stranded cut of a target nucleic acid. Accordingly, the term includes nickases and recombinases, as well as more conventional nucleases which cause single or double stranded breaks.

The method may comprise inserting a heterologous sequence in the CD163 gene at the target site. Such a heterologous DNA sequence can replace and/or disrupt the endogenous DNA sequence. This can be achieved by introducing a suitable template DNA molecule to the cell, such as single or double-stranded DNA molecule, which will be inserted by the cell's DNA repair mechanisms or an exogenous recombinase. Exemplary DNA sequences for insertion are described above, but many others could of course be used.

The genetically edited zygote can be grown to become an embryo and eventually an adult animal. As discussed above, if the editing event occurs in the single-cell zygote then all cells of this animal will therefore comprise the modified CD163 gene as all cells of the animal are derived from a single genetically edited cell. If the editing event occurs after one or more cell divisions then the resultant animal will likely be a mosaic for the editing event, in that it will have some cells derived from the edited cell and some cells derived from unedited cells.

The method may involve characterising the genetic modification which has occurred. Suitable methods to achieve this are set out below.

The method can be performed on a plurality of zygotes and the method may involve selecting zygotes in which the desired genetic modification has been achieved.

Preferably the nuclease comprises a pair of transcription activator-like effector nucleases (TALENs) or zinc finger nucleases (ZFNs). Such nucleases are well known in the art and comprise a nuclease moiety fused to a sequence-specific DNA binding moiety. The nuclease activity requires a pair of the nuclease moieties to form the active nuclease dimer. Such nucleases are well adapted to site-specific cleaving of DNA molecules, and techniques to target said nucleases to any desired sequences are known to the skilled person and described below. The TALENs or ZFNs can be tailored to target suitable sequences to achieve the desired DNA cut. By inducing a cut in the DNA the cell repairs the cut by NHEJ or HDR. The former is an error prone system and therefore can be used to introduce edits as a result of errors. The latter can be used to introduce a heterologous sequence into the cell.

Alternatively, the nuclease may comprise a nickase. Nickases are like TALENs or ZFNs in many ways, but they cause only a single strand break. This can be an advantage in inducing accurate homology-directed repair, which is particularly useful in the present invention to create a desired introgression. Nickases are described in Ramirez et al. 'Engineered zinc finger nickases induce homology-directed repair with reduced mutagenic effects' Nucleic Acids Research, 2012, 1-9 doi:10.1093/nar/gks179.

Another option is that the nuclease comprises a recombinase. Recombinases are a group of enzymes which allow very precise manipulation and editing of DNA. Although they are not currently as versatile as TALENs, ZFNs and nickases, they have significant potential to allow very tightly controlled editing events. Recombination controlled by recombinases can be used to accurately paste a sequence of interest into the CD163 gene.

Another option is that the nuclease comprises an RNA-guided site-specific nuclease, such as the CRISPR/Cas system described in Cong et al. 'Multiplex Genome Engineering Using CRISPR/Cas Systems', Science, 15 Feb. 2013: Vol. 339 no. 6121 pp. 819-823. Such systems use an RNA molecule to target a specific sequence in to be cleaved by the nuclease, in the case of the CRISPR/Cas system 'spacer' sequences are used to target the nuclease. Suitable spacers can be created and used to target the Cas nuclease to the desired location in the CD163 gene and thus cause double-stranded breaks in the DNA whereupon NHEJ would result in the introductions of indels.

Of course, in this rapidly developing field, other techniques for genetic editing are likely to become available. Such techniques could in many cases be readily adapted for use in the present invention.

Preferably the nuclease is adapted to target sequences in the region of the CD163 gene. The regions of particular interest are discussed in more detail above.

The site specific nuclease can be adapted to target a sequence which encodes domain 5 of CD163 or flanking intronic sequences (i.e. introns 6 and 7). For example the nuclease can target a sequence within exon 7 of the CD163 gene. Non-homologous end joining and/or homology-directed repair can then be utilised to edit the CD163 gene.

Two or more pairs of TALENs, ZFNs or other such nucleases can be adapted to excise a region of DNA.

For example, a suitable strategy involves delivering two TALEN pairs at the same time to engineer deletion (removal) of the 7th exon of the CD163 gene (which contains domain 5)

In certain embodiments the site specific nucleases are TALENs or ZFNs and are adapted to target the sequences:

```
(CD163 intron 6 target sequence)
                                       (SEQ ID NO 4)
5'-TCCCTCACCGAAATGCTATTTTCAGCCCACAGGAAACCCAGGCT
GGTTGGA-3'

(CD163 intron 7 target sequence)
                                       (SEQ ID NO 5)
5'-TCGGCGTAGTCTGCTCAAGTGAGACCCAGGGAATGTGTTCACTT
TGTTCCCA-3'
```

However, site specific nucleases adapted to target other suitable target sequences could of course be used.

In the above example, the following primers can suitably be used to detect editing events:

```
        forward
                                       (SEQ ID NO 6)
        5'-AAACCAAGAGGCATGAATGG-3' reverse
                                       (SEQ ID NO 7)
        5'-TGTCCCAGTGAGAGTTGCAG-3'
```

The method may comprise one or more of the step of testing the ability of the animal to tolerate challenge with a pathogen, e.g. a virus. For example, where the animal is a pig, the method may involve testing the ability of the genetically edited animal to survive infection with a highly virulent PRRS.

Relevant Definitions:

'Biologically active' in the present context can suitably refer to the ability of a fragment or variant to be bind to PRRSV. Fragments or variants may bind to PRRSV with higher or lower affinity than the bond between PRRSV and wild-type, membrane-bound CD163. It is preferred that the binding of PRRSV to the fragment or variant of CD163 is at least 50% as strong as between PRRSV and wild-type, membrane-bound CD163, more preferably at least 70%, 80%, 90%, 95% or 100% as strong. Bond strength in this case can be equated to the equilibrium constant $K_d$ of the relevant interaction in a suitable medium, e.g. serum or serum equivalent.

However, in several embodiments of the present invention (particularly in the case of 'decoy' proteins adapted to interfere with PRRSV infection), the most appropriate definition for a 'biological activity' is the ability of a given isolated or synthetic protein of the present invention to prevent or inhibit PRRSV infection of macrophages, preferably porcine macrophages, such as MARC-145 cells (see section 5 of Example 1 below for an appropriate in vitro test). Accordingly, an alternative and appropriate definition for 'biologically active' in the context of fragments or variants derived from the extracellular portion of CD163 is the ability of a given isolated or synthetic protein of the present to interfere with PRRSV infection and therefore reduce or inhibit infectivity of PRRSV assay. It appears that inhibition of infection can occur even where binding of an isolated or synthetic protein of the present invention is not readily detectable in vitro (such as with proteins containing only domain 5); this may possibly be a result of typical in vitro conditions poorly replicating the in vivo environment, and this could possibly be addressed with improved in vitro assays. Nevertheless, a test which directly determines the ability of a given synthetic or isolated protein to interfere with PRRSV infection represents a 'gold standard'. A suitable assay to determine the 'biological activity' of a given fragment or variant allows the skilled person to assess the ability of a given protein to affect the ability of PRRSV to infect macrophages, especially porcine macrophages; an exemplary assay is set out in section 5 of Example 1. Carrying out such an assay allows the skilled person to determine whether any given protein, fragment or variant is potentially useful as an anti-PRRSV therapeutic. A reduction of infectivity by at least 30%, more preferably at least 50%, yet more preferably at least 60%, 70%, 80% or 90% compared with a control. Infectivity can be quantitatively determined, and percentage changes in infectivity thereby calculated, by measuring PRRSV viral nucleoprotein levels in suitable cells exposed to PRRSV under suitable conditions, e.g. via an ELISA or other well-known techniques.

'Conservative' changes or substitutions, as used herein, refer to one or more amino acid substitutions (for example of 1, 2, 5 or 10 residues) for amino acid residues having similar biochemical properties. Typically, conservative substitutions have little to no impact on the activity of a resulting polypeptide. For example, a conservative substitution in a contact phase factor inhibitory peptide may be an amino acid substitution that does not substantially affect the ability of the peptide to inhibit a contact phase factor or combination thereof. Screening of variants can be used to identify which amino acid residues can tolerate an amino acid substitution.

In one example, one conservative substitution is included in the protein. In another example, 10 or fewer conservative substitutions are included in the protein, such as five or fewer. A protein of the invention may therefore include 1, 2, 3, 4, 5, 6, 7, 8, 9 10 or more conservative substitutions. A polypeptide can be produced to contain one or more conservative substitutions by manipulating the nucleotide sequence that encodes that polypeptide using, for example, standard procedures such as site-directed mutagenesis or PCR. Alternatively, a polypeptide can be produced to contain one or more conservative substitutions by using peptide synthesis methods, for example as known in the art.

Substitutional variants are those in which at least one residue in the amino acid sequence has been removed and a different residue inserted in its place. Examples of amino acids which may be substituted for an original amino acid in a protein and which are regarded as conservative substitutions include: Ser for Ala; Lys for Arg; Gln or His for Asn; Glu for Asp; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val. In one embodiment, the substitutions are among Ala, Val Leu and Ile; among Ser and Thr; among Asp and Glu; among Asn and Gln; among Lys and Arg; and/or among Phe and Tyr. Further information about conservative substitutions can be found in, among other locations, Ben-Bassat et al., (J. Bacteriol. 169:751-7, 1987), O'Regan et al., (Gene 77:237-51, 1989), Sahin-Toth et al., (Protein Sci. 3:240-7, 1994), Hochuli et al., (Bio/Technology 6:1321-5, 1988), WO 00/67796 (Curd et al.) and in standard textbooks of genetics and molecular biology.

By the term "Fc" or "Fc fragment" it is intended to refer to a region of an antibody molecule that binds to antibody receptors on the surface of cells such as macrophages and mast cells, and to complement protein. Fc (50,000 daltons) fragments contain the CH2 and CH3 region and part of the hinge region held together by one or more disulfides and noncovalent interactions. Fc and Fc5p fragments are produced from fragmentation of IgG and IgM, respectively. The term Fc is derived from the ability of these antibody fragments to crystallize. Fc fragments are generated entirely from the heavy chain constant region of an immunoglobulin. The Fc fragment cannot bind antigen, but it is responsible for the effector functions of antibodies, such as complement fixation.

"Fusion protein", as used herein, refers to a protein containing amino acid sequences from each of two distinct proteins; it is formed by the expression of a recombinant gene in which two coding sequences have been joined together such that their reading frames are in phase. Hybrid genes of this type may be constructed in vitro in order to label the product of a particular gene with a protein that can be more readily assayed. For example, a protein may be linked to a signal peptide to allow its secretion by the cell, or linked a peptide to promote stability of efficacy.

"Genetically edited" or "genetically modified" when used in relation to subject biological material, refers to the fact that the subject biological material has been treated to produce a genetic modification thereof compared to control, e.g. wild type, biological material.

The term "isolated" means a biological component (such as a nucleic acid molecule or protein) that has been substantially separated or purified away from other biological components in the cell of the organism in which the component naturally occurs, i.e., other chromosomal and extrachromosomal DNA and RNA, and proteins. Nucleic acids and proteins that have been "isolated" include nucleic acids and proteins purified by standard purification methods. The term also embraces nucleic acids and proteins prepared by recombinant expression in a host cell as well as chemically synthesized nucleic acids, proteins and peptides.

"Protein" and "peptide", as used herein, can be used interchangeably (unless the context suggests otherwise) and mean at least two covalently attached amino acids linked by a peptidyl bond. The term protein encompasses purified natural products, or products which may be produced partially or wholly using recombinant or synthetic techniques. The terms peptide and protein may refer to an aggregate of a protein such as a dimer or other multimer, a fusion protein, a protein variant, or derivative thereof. A protein may comprise amino acids not encoded by a nucleic acid codon, i.e. non-natural amino acids.

The terms "prophylaxis" or "prevention of infection" includes reference to treatment therapies for the purpose of preserving health or inhibiting or delaying the initiation and/or progression of an event, state, disorder or condition, for example for the purpose of reducing the chance of an event, state, disorder or condition occurring. The outcome of the prophylaxis may be, for example, preservation of health or delaying the initiation and/or progression of an event, state, disorder or condition. It will be recalled that, in any individual subject or even in a particular subject population, a treatment may fail, and this paragraph is to be understood accordingly.

"Protein modification", as used herein, is a type of protein variant and means an alteration to a moiety chemically linked to a protein. For example, a modification may be an altered carbohydrate or PEG structure attached to a protein. The proteins of the invention may include at least one such protein modification. The term includes modifications of the protein, for example, protein modified by glycosylation, acetylation, phosphorylation, pegylation, ubiquitination, and so forth.

"Site-directed mutagenesis", as used herein, refers to the in vitro induction of mutagenesis at a specific site in a given target nucleic acid molecule.

The term "treatment", and the therapies encompassed by this invention, include the following and combinations thereof: (1) inhibiting, e.g. delaying initiation and/or progression of, an event, state, disorder or condition, for example arresting, reducing or delaying the development of the event, state, disorder or condition, or a relapse thereof in case of maintenance treatment or secondary prophylaxis, or of at least one clinical or subclinical symptom thereof; (2) preventing or delaying the appearance of clinical symptoms of an event, state, disorder or condition developing in an animal (e.g. a pig) that may be afflicted with or predisposed to the state, disorder or condition but does not yet experience or display clinical or subclinical symptoms of the state, disorder or condition; and/or (3) relieving and/or curing an event, state, disorder or condition (e.g., causing regression of the event, state, disorder or condition or at least one of its clinical or subclinical symptoms, curing a patient or putting a patient into remission). The benefit to a subject to be treated may be either statistically significant or at least perceptible to the subject or to the veterinarian. It will be understood that a medicament will not necessarily produce a clinical effect in each subject to whom it is administered; thus, in any individual subject or even in a particular patient population, a treatment may fail or be successful only in part, and the meanings of the terms "treatment", "prophylaxis" and "inhibitor" and of cognate terms are to be understood accordingly. The invention concerns, amongst other things, the treatment of PRRS. The compositions and methods described herein are of use for therapy and/or prophylaxis of the mentioned conditions.

"Variants" of a protein or peptide, as used herein, refers to a protein resulting when a polypeptide is modified by one or more amino acids (e.g. insertion, deletion or substitution), or which comprises a protein modification, or which contains modified or non-natural amino acids. The variant may have "conservative" changes, wherein a substituted amino acid has similar structural or chemical properties. More rarely, a variant may have "non-conservative" changes, for example, replacement of a glycine with a tryptophan. Variants may also include sequences with amino acid deletions or insertions, or both. Guidance in determining which amino acid residues may be substituted, inserted, or deleted without abolishing biological or immunological activity may be found using computer programs well known in the art.

Protein variants according to the present invention can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable caution or esterified, for example to form a C1-C6 alkyl ester, or converted to an amide, for example of formula CONR1R2 wherein R1 and R2 are each independently H or C1-C6 alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to C1-C6 alkyl or dialkyl amino or further converted to an amide. Hydroxyl groups of the peptide side chains may be converted to alkoxy or ester groups, for example C1-C6 alkoxy or C1-C6 alkyl ester, using well-recognized techniques. Phenyl and phenolic rings of the peptide side chains may be substituted with one or more halogen atoms, such as F, Cl, Br or I, or with C1-C6 alkyl, C1-C6 alkoxy, carboxylic acids and esters thereof, or amides of such carboxylic acids. Methylene groups of the peptide side chains can be extended to homologous C2-C4 alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability.

"Vector", as used herein, refers to a self-replicating DNA or RNA molecule that transfers a nucleic acid segment between cells.

"Virion", as used herein, refers to a particle composed of viral RNA and viral capsid protein.

The invention will now be further described, by way of example only, with reference to the accompanying figures in which.

Figure 5:
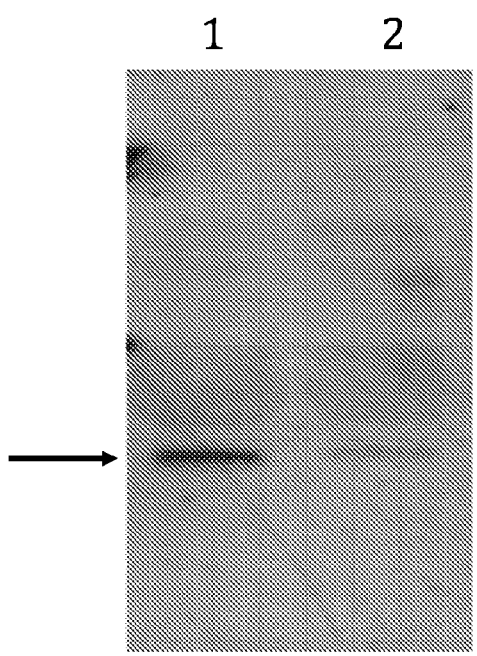
Figure 6:
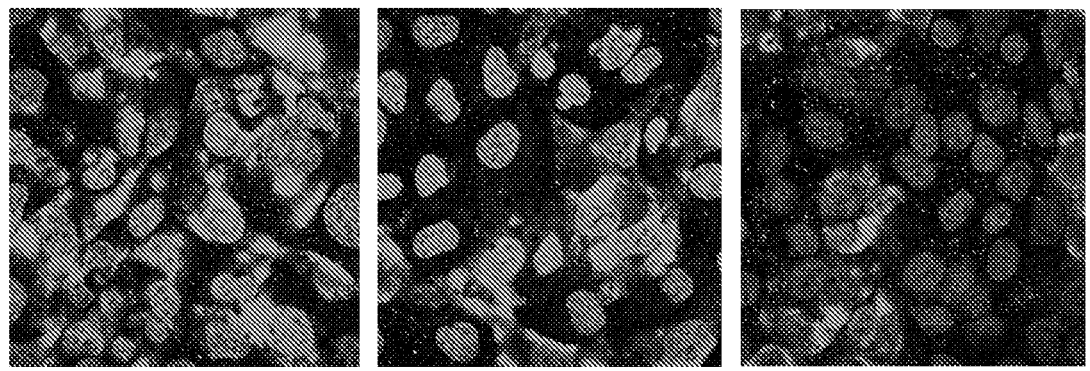
Figure 6:
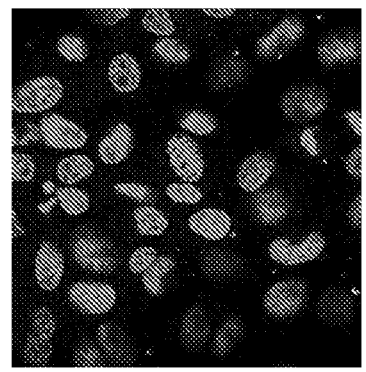

FIG. 5 shows immunodetection of D55-Fc fusion protein in CHO (lane 1) and MARC-145 (lane 2) recombinant cells FIG. 6 shows microscopic images PRRSV Infection of recombinant MARC-145 cells. PRRSV (pink staining) are detected in the cytosol of D14-Fc, D59-Fc and pFuse control cells but not in 3 fields of D55-Fc cells. Nuclei are stained blue.

FIG. 7: PRRSV viral load in the growth medium 24, 48, 72 and 120 hours post infection. PRRSV GP5 RNA was detected using Sybrgreen RTPCR.

EXAMPLES

Example 1—In Vitro Production and Testing of Decoy CD163 Fragments

1—RTPCR of Porcine CD163 SRCR Domains

Figure 1:
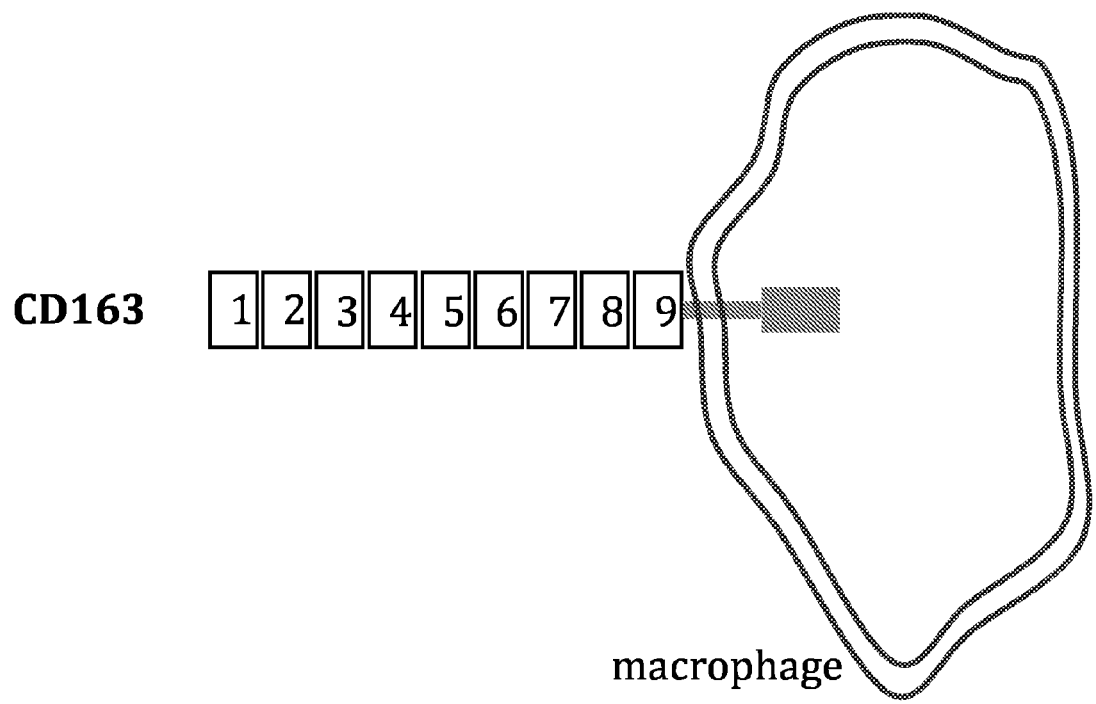
FIG. 1 illustrates CD163 expressed on the cell surface of the alveolar macrophage
Figure 1A:
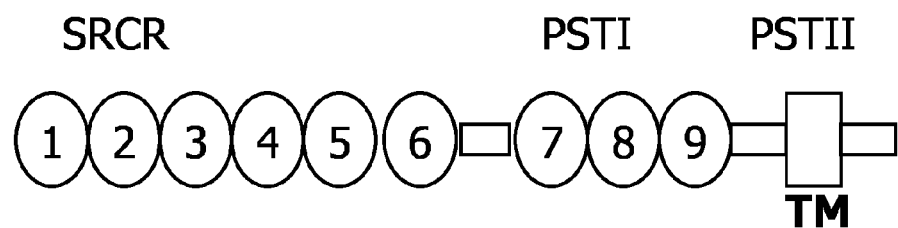
FIG. 1a is a schematic representation of CD163 protein
Figure 2:
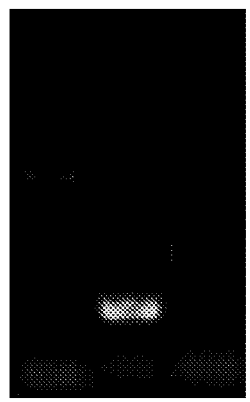
FIG. 2 shows the result of the RT-PCR amplification of domains D14, D55 and D59

To generate cDNA fragment that encodes domain of the scavenger receptor CD163 (FIG. 1 and FIG. 1a) we have used the published sequence GeneBank accession # ABV80230. Tables 1 and 2 show the primer sequences and their combination that were employed for the reverse transcriptase and PCR stages. Domains of cD163 were cloned using RNA prepared from porcine alveolar macrophage isolated from lung macrophage of a Large White breed #131 (Ait-Ali et al. 2007). Reverse transcriptase and PCR were performed as described elsewhere (Ait-Ali et al. 2007) and the result is shown in FIG. 2.

TABLE 1

| Primers | Sequence |
| --- | --- |
| D1-FW | ACGAATTCCAGAATGGTGCTACATGAAAACTCTGG (SEQ ID NO 8) |
| D5-FW | TCGATATCACACAGGAAACCCAGGCTGGTTGGAGG (SEQ ID NO 9) |
| D4-RV | GCCGATATCGCTGAGCAGGTAATTTTGGCTTCGTC (SEQ ID NO 10) |
| D5-RV | TAACCATGGTGTATCTTGAGCAGACTACGCCGACG (SEQ ID NO 11) |
| D9-RV | CCGATATCGAGCACGTCACAGCAGCATCCTCCTTG (SEQ ID NO 12) |

TABLE 2

| Decoy domains | Size (bp) | Forward primer | Reverse primer | Restriction digestion |
| --- | --- | --- | --- | --- |
| (D14) 1-2-3-4 | 1215 | D1-FW | D4-RV | EcoR and EcoRV |
| (D55) 5 | 303 | D5-FW | D5-RV | EcoRV and NcoI |
| (D59) 5-6-7-8-9 | 1521 | D5-FW | D9-RV | EcoRV |

2—Cloning of CD 163 Domains

Figure 3:
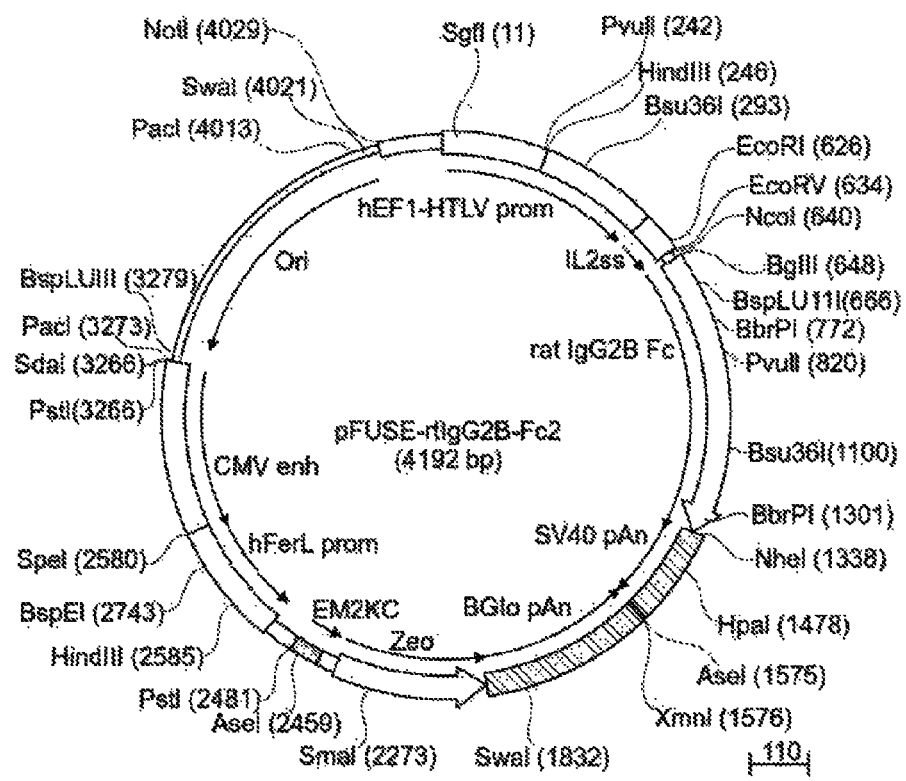
FIG. 3 shows a schematic of the cloning vector pFUSE-rtIgG2B-Fc2
Figure 4:
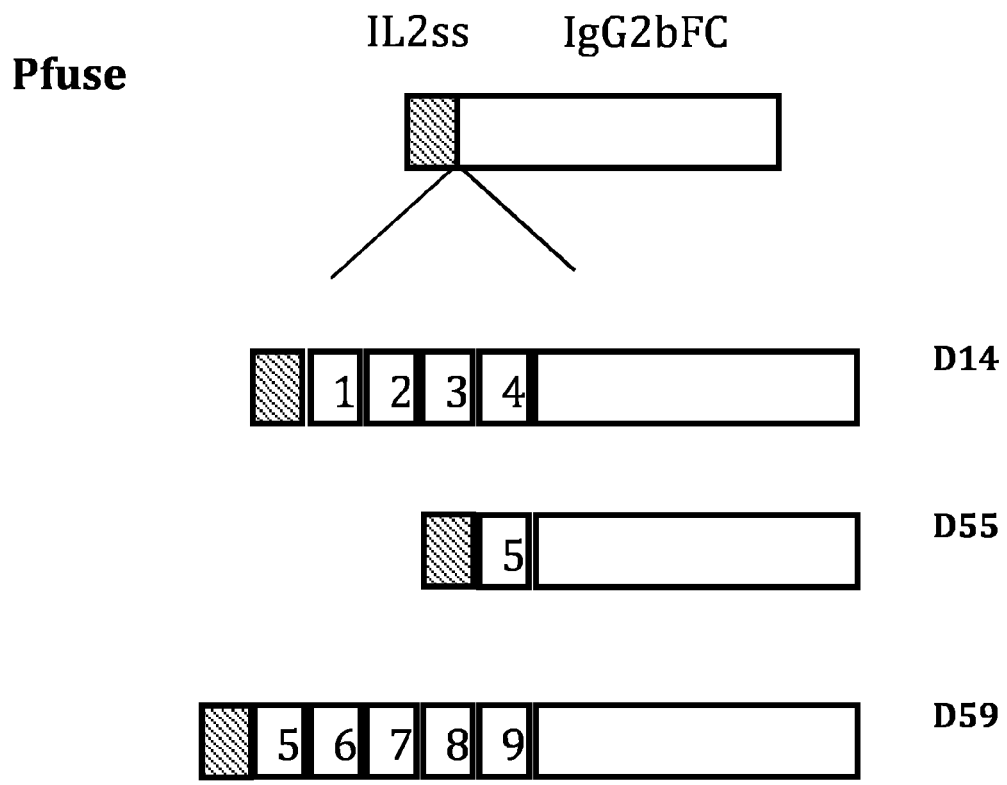
FIG. 4 shows a schematic representation of the Fc fusion proteins

Decoy domains D14, D55 and D59 were cloned into the expression vector pFUSE-rtIgG2B-Fc2 (FIG. 3, Novagen) into the multi-cloning site and between the IL2ss secretory sequence and the rat-IgG2B Fc region to generate soluble Fc fusion proteins as shown in FIG. 4. IL2-D55-FC refers to a fusion IL2ss, domain 5 and rat-IgG2B Fc. The accuracy of the fusion constructs were verified using Sanger sequencing.

The nucleotide sequence encoding IL2-D55-FC (D55 encoding region in lower case) is:

(SEQ ID NO 14)
ATGTACAGGATGCAACTCCTGTCTTGCATTGCACTAAGTCTTGCACT

TGTCACGAATTCGATATCcaggaaacccaggctggttggaggggaca ttccctgctctggtcgtgttgaagtacaacatggagacacgtgggc accgtctgtgattctgacttctctctggaggcggccagcgtgctgtg cagggaactacagtgcggcactgtggtttccctcctgggggagctc actttggagaaggaagtggacagatctgggctgaagaattccagtgt gaggggcacgagtcccacctttcactctgcccagtagcaccccgccc tgacgggacatgtagccacagcagggacgtcggcgtagtctgctcaa gatacacCATGGTTAGATCTCCTACATGCCCTACATGTCACAAATGC

CCAGTTCCTGAACTCTTGGGTGGACCATCTGTCTTCATCTTCCCGCC

AAAGCCCAAGGACATCCTCTTGATCTCCCAGAACGCCAAGGTCACGT

GTGTGGTGGTGGATGTGAGCGAGGAGGAGCCGGACGTCCAGTTCAGC

TGGTTTGTGAACAACGTAGAAGTACACACAGCTCAGACACAACCCCG

TGAGGAGCAGTACAACAGCACCTTCAGAGTGGTCAGTGCCCTCCCCA

TCCAGCACCAGGACTGGATGAGCGGCAAGGAGTTCAAATGCAAGGTC

AACAACAAAGCCCTCCCAAGCCCCATCGAGAAAACCATCTCAAAACC

CAAAGGGCTAGTCAGAAAACCACAGGTATACGTCATGGGTCCACCGA

CAGAGCAGTTGACTGAGCAAACGGTCAGTTTGACCTGCTTGACCTCA

GGCTTCCTCCCTAACGACATCGGTGTGGAGTGGACCAGCAACGGGCA

TATAGAAAAGAACTACAAGAACACCGAGCCAGTGATGGACTCTGACG

GTTCTTTCTTCATGTACAGCAAGCTCAATGTGGAAAGGAGCAGGTGG

GATAGCAGAGCGCCCTTCGTCTGCTCCGTGGTCCACGAGGGTCTGCA

CAATCACCACGTGGAGAAGAGCATCTCCCGGCCTCCGGGTAAATGA

3—Generation of CHO and MARC-145 Recombinant Cells

D14-FC, D55-FC, D59-Fc constructs and the empty pFUSE vector (negative control) were transfected into MARC-145 and CHO cells using Lipofectamine 2000 (Invitrogen™) and stable transfected cells were selected with Zeocin antibiotic (data not shown).

4—Detection of the Expression of D55-Fc Protein

D55-Fc expression was detected in growth medium of D55-Fc in recombinant CHO and MARC-145 cells. FIG. 5 shows the western blot detection of the D55-Fc using goat anti-rat IgG2b antibody. The integrity of the D55-Fc RNA expressed in the recombinant cells was confirmed using RT-PCR and Sanger sequencing (data not shown).

5—PRRSV Infectivity

Recombinant MARC-145 cells were challenged with the European PRRSV strain Olot/91 at multiplicity of infection (moi) of 1 for 40 hours. Cells were then fixed and PRRSV viral nucleoprotein was detected using antibody SDOW17 and the secondary antibody goat anti-mouse IgG-Alexa Fluor-647 (FIG. 6). This experiment was repeated 3 times using different batches of virus.

To test if the PRRSV virus RNA can be detected in the growth medium of infected cells, recombinant Marc cells were challenged with the European PRRSV strain Olot/91 at moi of 1 and the virus RNA was monitored in the medium 24, 48, 72, 120 hours post infection using RTPCR. FIG. 7 shows that in contrast to D55-Fc cells the Ct declined drastically in Pfuse, D14-Fc and D59-Fc cells. This experiment was repeated twice with independent virus preparation. Taken together these results suggest that the D55-Fc MARC145 cells were less susceptible to PRRSV than other cells.

6—D55-Fc MARC Cells Transfection with a PRRSV Infectious Clone

To test that D55-Fc Marc cells reduced susceptibility is due to a blockade of the viral rather than an increase of immunity of the recombinant cells, D55-Fc MARC145 cells were transfected with an infectious clone SD01-08-GFP that expresses PRRSV-GFP. Results showed that the recombinant cells expressed GFP-PRRSV similarly to the non-recombinant cells. This experiment suggests strongly that the phenotype of recombinant D55-Fc cells is probably associated to a blockade of viral entry rather than an increase of immunity.

Example 2—Creation of a Pig Over-Expressing Domain 5 Using a Lentiviral Vector Lentiviral vectors are produced by co-transfection of HEK293T cells with 3 plasmids; the first encodes a chosen promoter (this could be ubiquitous, e.g. the CAG promoter, tissue restricted, e.g. the CMV immediate early promoter which is known to be expressed predominantly in exocrine cells, or tissue specific, e.g. CSF1 receptor promoter which is specific to cells of the mononuclear macrophage lineage or a synthetic liver specific promoter) directing expression of a transgene comprised of exon7 (domain 5) fused to a secretory signal peptide such as that from IL-2. This promoter-exon 7 combination is flanked by HIV1 regulatory sequence elements and inverted terminal repeats. The second plasmid encodes HIV1 Gag and PoI elements, such as those encoded by plasmid psPAX2. The third plasmid encodes a version of the vesicular stomatitis virus G protein that is commonly used to pseudotype lentiviral particles due to its broad host tropism.

Once transfected into HEK293T cells these plasmids result in the production of replication defective lentiviral particles will be secreted from the cells into the culture medium. Lentiviral particles are recovered from the medium by (for example) ultracentrifugation.

Transgenic pigs are produced by injection of a suspension of the lentiviral particles into the perivitelline space of the fertilised egg (zygote). Typically embryos are produced from Large-White gilts that are approximately 9 months of age and weigh at least 120 kg at time of use. Super-ovulation is achieved by feeding, between day 11 and 15 following an observed oestrus, 20 mg altrenogest (Regumate, Hoechst Roussel Vet Ltd) once daily for 4 days and 20 mg altrenogest twice on the 5th day. On the 6th day, 1500 IU of eCG (PMSG, Intervet UK Ltd) is injected at 20:00 hrs. Eighty three hours later 750 IU hCG (Chorulon, Intervet UK Ltd) is injected. Donor gilts are inseminated twice 6 hours apart after exhibiting heat generated following super-ovulation. Zygotes are surgically recovered from mated donors by mid-line laparotomy under general anesthesia on day 1 following oestrus into NCSU-23 HEPES base medium. Zygotes are subjected to an injection of between 50-1000 pl injection of lentiviral particle suspension into the perivitelline space. Recipient females are treated identically to donor gilts but remain un-mated. Following lentiviral injection, zygotes are transferred to recipient gilts following a mid-line laparotomy under general anesthesia. During surgery, the reproductive tract is exposed and zygotes transferred into the oviduct of recipients using a 3.5 French gauge tomcat catheter.

Example 3—Creation of a Pig Overexpressing Domain 5 Using DNA Editor-Mediated Targeting DNA editors (TALENS, ZFNs or CRISPRs) to a target site in the porcine genome can be constructed through known techniques.

This could, for example, be the porcine ROSA26 locus or a similar locus where robust gene expression is anticipated (see, for example, CN102851279 for details of a pig ROSA26 locus).

A DNA molecule comprised of a promoter directing expression of exon7 (domain 5) fused to a secretory signal peptide as detailed above, flanked by sequence of 30-2000 bp immediately upstream and downstream of the DNA editor target site in the porcine genome can be designed and constructed using known techniques (henceforth referred to as the targeting construct).

Porcine zygotes produced as above will be injected into either the cytoplasm or a pronucleus with a solution comprising the targeting construct together with the DNA editor supplied in either DNA, RNA or protein form. Injected zygotes will be transferred to recipient sows as above.

Example 4—Editing of CD163 Locus Using Genome Editing Technologies

Example 4a—Editor Design and Construction

Editing of the CD163 locus can be achieved using DNA editor technology (e.g. TALEN, ZFN, CRISPR/Cas9). This is illustrated through TALEN methodology. TALENs are designed using the TALE-NT software and assembled using methods described in Cermak et al (2011). Briefly, intermediary arrays are produced for each TALEN pair that are compatible for Golden Gate cloning into pC-+63-TAL modified vector (although other vectors such as pC-+231-TAL, RCIscript-+231-TAL, pC-GoldyTALEN or RCIscript-GoldyTALEN can be used. Arrays are joined in the above vectors as follows; 150 ng each pFUS_A, pFUS_B, pLR-X and the desired backbone are mixed in a 20 μl digestion/ligation reaction including 50 units T4 DNA ligase (New England Biolabs) and 10 units Esp3l (Fermentas) in 1× T4 ligase buffer (New England Biolabs). The reaction is incubated in a thermocycler for 10 cycles of 5 min at 37° C. and 10 min at 16° C., then heated to 50° C. for 5 min and then 80° C. for 5 min. Two microliters of each reaction is transformed into *E. coli* and plated on LB-carbenicillin plates. Plasmid DNA is purified and mRNA synthesized from SacI linearized RCIscript vectors using the mMessage Machine T3 Kit (Ambion).

Example 4b—Target Site Details

With the intention of deleting CD163 exon 7 from the pig genome, target sites located upstream (e.g. in intron 6) or downstream (e.g. in intron 7) are selected.

For example, the TALENs can target the following sequences:

```
(CD163 intron 6 target sequence)
                                       (SEQ ID NO 4)
5'-TCCCTCACCGAAATGCTATTTTCAGCCCACAGGAAACCCAGGCT
GGTTGGA-3'

(CD163 intron 7 target sequence)
                                       (SEQ ID NO 5)
5'-TCGGCGTAGTCTGCTCAAGTGAGACCCAGGGAATGTGTTCACTT
TGTTCCCA-3'
```

Other suitable target sequences could of course be used.

In the above example, the following primers can be used to detect and analyse editing events:

```
    forward
                                       (SEQ ID NO 6)
    5'-AAACCAAGAGGCATGAATGG-3' reverse
                                       (SEQ ID NO 7)
    5'-TGTCCCAGTGAGAGTTGCAG-3'
```

Example 4c—Generation of Gene Edited Pigs

Gene edited pigs are produced through injection of the TALEN (or another DNA editor) into the fertilised egg (zygote). Delivery can be to the nucleus or cytoplasm of the zygote. The TALEN can be delivered as DNA, RNA or protein. To illustrate the approach the method of cytoplasmic delivery of a TALEN is given.

Embryos are produced from Large-White gilts that are approximately 9 months of age and weigh at least 120 kg at time of use. Super-ovulation is achieved by feeding, between day 11 and 15 following an observed oestrus, 20 mg altrenogest (Regumate, Hoechst Roussel Vet Ltd) once daily for 4 days and 20 mg altrenogest twice on the 5th day. On the 6th day, 1500 IU of eCG (PMSG, Intervet UK Ltd) is injected at 20:00 hrs. Eighty three hours later 750 IU hCG (Chorulon, Intervet UK Ltd) is injected. Donor gilts are inseminated twice 6 hours apart after exhibiting heat generated following super-ovulation. Embryos are surgically recovered from mated donors by mid-line laparotomy under general anesthesia on day 1 following oestrus into NCSU-23 HEPES base medium. Embryos are subjected to a single 2-5 pl cytoplasmic injection of TALEN pair mRNA at 2 ng/pl. Recipient females are treated identically to donor gilts but remained un-mated. Following TALEN injection, fertilized embryos are transferred to recipient gilts following a mid-line laparotomy under general anesthesia. During surgery, the reproductive tract is exposed and embryos are transferred into the oviduct of recipients using a 3.5 French gauge tomcat catheter.

Example 4d: Genotyping of Editing Events in Pigs

Gene editing events in born piglets are identified by direct sequencing of amplified, isolated DNA (e.g. using the primers set out above) and through gel electrophoresis assay. The latter identified mismatch between the two alleles through digestion by the Cel1 enzyme.

The DNA is extracted from tissue samples (e.g. ear skin biopsy) using the Fast Tissue-to-PCR kit, Fermentas. The Fast tissue DNA sample is then used as a template for High fidelity PCR (AccuPrime™ Taq DNA Polymerase High Fidelity, Invitrogen™) using primers designed to amplify across CD163 exon 7 and neighbouring genomic region (as set out above, for example). The PCR product is then sent for sequence analysis to allow identification of editing events. Alternatively the PCR products are cloned into a plasmid and individual clones sequenced allowing heterozygous and mosaic editing events to be analysed separately. Alternatively the deletion of CD163 exon 7 can be identified by standard Southern blotting with appropriate restriction enzymes.

Nucleotide and Peptide Sequences for CD163

```
GeneBank accession # ABV80230- CD163 protein- exon 7, which
encodes domain 5, is underlined.
                                                     (SEQ ID NO 1)
   1   mdklrmvlhe  nsgsadfrrc  sahlssftfa  vvavlsaclv  tsslggkdke  lrltggenkc 61   sgrvevkvqe  ewgtvcnngw  dmdvvsvvcr  qlgcptaika  tgwanfsags  griwmdhvsc 121   rgnesalwdc  khdgwgkhnc  thqqdagvtc  sdgsdlemrl  vnggnrclgr  ievkfqgrwg 181   tvcddnfnin  hasvvckqle  cgsaysfsgs  anfgegsgpi  wfddlvcngn  esalwnckhe 241   gwgkhncdha  edagviclng  adlklrvvdg  vtecsgrlev  kfqgewgtic  ddgwdsddaa 301   vackqlgcpt  avtaigrvna  segtghiwld  syschghesa  lwqcrhhewg  khycnhneda 361   gvtcsdgsdl  elrlkgggsh  cagtveveiq  klvgkvcdrs  wglkeadvvc  rqlgcgsalk 421   tsyqvysktk  atntwlfvss  cngnetslwd  cknwqwggls  cdhydeakit  csahrkprlv 481   qgdipcsqry  evqhqdtwqt  vcdsdfslea  asvlcrelqc  qtvvsllqqa  hfqeqsqqiw 541   aeefqceqhe  shlslcpvap  rpdqtcshsr  dvqvvcsryt  qirivngktp  cegrvelnil 601   gswgslcnsh  wdmedahvlc  qqlkogvals  iprgapfgkg  seqvwrhmfh  ctgtekhmgd 661   csvtalgasl  cssgqvasvi  csgnqsqtls  pcnssssdps  ssiiseengv  acigsgqlrl 721   vdgggrcagr  vevyhegswg  ticddswdln  dahvvckqls  cgwainatgs  ahfgegtgpi 781   wldeincngk  eshiwqchsh  gwgrhncrhk  edagvicsef  mslrlisens  retcagrlev 841   fyngawgsvg  rnsmspatvg  vvcrqlgcad  rgdispassd  ktvsrhmwvd  nvqcpkgpdt 901   lwqcpsspwk  krlaspseet  witcankirl  qegntncsgr  veiwyggswg  tvcddswdle
```

-continued

```
 961  daqvvcrqlg cgsaleagke aafgqgtgpi wlnevkckgn etslwdcpar swghsdcghk
1021  edaavtcsei aksreslhat grssfvalai fgvillacli afliwtqkrr qrqrlsvfsg
1081  gensvhqiqy remnsclkad etdmlnpsgd hsevq
```

NCBI Reference Sequence: NM_213976.1- CD163 mRNA sequence (SEQ ID NO 2)

```
   1  atggtgctac ttgaagactc tggatctgca gactttagaa gatgttctgc ccatttaagt
  61  tccttcactt ttgctgtagt cgctgttctc agtgcctgct tggtcactag ttctcttgga
 121  ggaaaagaca aggagctgag gctaacgggt ggtgaaaaca gtgctctgg aagagtggag
 181  gtgaaagtgc aggaggagtg gggaactgtg tgtaataatg ctgggacat ggatgtggtc
 241  tctgttgttt gtaggcagct gggatgtcca actgctatca aagccactgg atgggctaat
 301  tttagtgcag gttctggacg catttggatg gatcatgttt cttgtcgagg aatgagtca
 361  gctctctggg actgcaaaca tgatggatgg ggaaagcata actgtactca ccaacaggat
 421  gctggagtaa cctgctcaga tggatctgat ttagagatga ggctggtgaa tggaggaaac
 481  cggtgcttag aagaataga agtcaaattt caagagcggt ggggaacagt gtgtgatgat
 541  aacttcaaca taaatcatgc ttctgtggtt tgtaaacaac ttgaatgtgg aagtgctgtc
 601  agtttctctg gttcagctaa ttttggagaa ggttctggac caatctggtt tgatgatctt
 661  gtatgcaatg gaatgagtc agctctctgg aactgcaaac atgaaggatg gggaaagcac
 721  aattgcgatc atgctgagga tgctggagtg atttgcttaa atggagcaga cctgaaactg
 781  agagtggtag atggactcac tgaatgttca ggaagattgg aagtgaaatt ccaaggagaa
 841  tggggaacaa tctgtgatga tggctgggat agtgatgatg ccgctgtggc atgtaagcaa
 901  ctgggatgtc caactgctgt cactgccatt ggtcgagtta acgccagtga gggaactgga
 961  cacatttggc ttgacagtgt ttcttgccat ggacacgagt ctgctctctg gcagtgtaga
1021  caccatgaat ggggaaagca ttattgcaat cataatgaag atgctggtgt gacatgttct
1081  gatggatcag atctggaact gagacttaaa ggtggaggca gccactgtgc tgggacagtg
1141  gaggtggaaa ttcagaaact ggtaggaaaa gtgtgtgata agctgggg actgaaagaa
1201  gctgatgtgg tttgcaggca gctgggatgt ggatctgcac tcaaaacatc atatcaagtt
1261  tattccaaaa ccaaggcaac aaacacatgg ctgtttgtaa gcagctgtaa tggaaatgaa
1321  acttctcttt gggactgcaa gaattggcag tggggtggac ttagttgtga tcactatgac
1381  gaagccaaaa ttacctgctc agcccacagg aaacccaggc tggttggagg ggacattccc
1441  tgctctggtc gtgttgaagt acaacatgga gacacgtggg gcaccgtctg tgattctgac
1501  ttctctctgg aggcggccag cgtgctgtgc agggaactac agtgcggcac tgtggtttcc
1561  ctcctggggg gagctcactt tggagaagga agtggacaga tctgggctga agaattccag
1621  tgtgagggc acgagtccca cctttcactc tgcccagtag caccccgccc tgacgggaca
1681  tgtagccaca gcagggacgt cggcgtagtc tgctcaagat acacacaaat ccgcttggtg
1741  aatggcaaga ccccatgtga aggaagagtg gagctcaaca ttcttgggtc ctgggggtcc
1801  ctctgcaact ctcactggga catggaagat gcccatgttt tatgccagca gcttaaatgt
1861  ggagttgccc tttctatccc gggaggagca cctttggga aaggaagtga gcaggtctgg
1921  aggcacatgt tcactgcac tgggactgag aagcacatgg gagattgttc cgtcactgct
1981  ctgggcgcat cactctgttc ttcagggcaa gtggcctctg taatctgctc agggaaccag
2041  agtcagacac tatccccgtg caattcatca tcctcggacc catcaagctc tattatttca
2101  gaagaaagtg gtgttgcctg catagggagt ggtcaacttc gcctggtcga tggaggtggt
```

-continued

```
2161  cgttgtgctg ggagagtaga ggtctatcct ggggcatcct ggggcaccat ctgtgatgac
2221  agctgggacc tgaatgatgc ccatgtggtg tgcaaacagc tgagctgtgg atgggccatt
2281  aatgccactg gttctgctca ttttggggaa ggaacagggc ccatttggct ggatgagata
2341  aactgtaatg gaaaagaatc tcatatttgg caatgccact cacatggttg ggggcggcac
2401  aattgcaggc ataaggagga tgcaggagtc atctgctcag agttcatgtc tctgagactg
2461  atcagtgaaa acagcagaga gacctgtgca gggcgcctgg aagttttta caacggagct
2521  tggggcagcg ttggcaggaa tagcatgtct ccagccacag tggggtggt atgcaggcag
2581  ctgggctgtg cagacagagg ggacatcagc cctgcatctt cagacaagac agtgtccagg
2641  cacatgtggg tggacaatgt tcagtgtcct aaaggacctg acacactatg gcagtgcccc
2701  tcatctccat ggaagaagag actggccagc ccctcagagg agacatggat cacatgtgcc
2761  aacaaaataa gacttcaaga aggaaacact aattgttctg gacgtgtgga gatctggtac
2821  ggaggttcct ggggcactgt gtgtgacgac tcctgggacc ttgaagatgc tcaggtggtg
2881  tgccgacagc tgggctgtgc ctcagctttg gaggcaggaa agagcccgc atttggccag
2941  gggactgggc ccatatggct caatgaagtg aagtgcaagg ggaatgaacc ctccttgtgg
3001  gattgtcctg ccagatcctg gggccacagt gactgtggac acaaggagga tgctgctgtg
3061  acgtgctcag aaattgcaaa gagccgagaa tccctacatg ccacaggtcg ctcatctttt
3121  gttgcacttg caatctttgg ggtcattctg ttggcctgtc tcatcgcatt cctcatttgg
3181  actcagaagc gaagacagag gcagcggctc tcagttttct caggaggaga gaattctgtc
3241  catcaaattc aataccggga gatgaattct tgcctgaaag cagatgaaac ggatatgcta
3301  aatccctcag gagaccactc tgaagtacaa tgaaaaggaa aatgggaatt ataacctggt
3361  gagttcagcc tttaagatac cttgatgaag acctggacta
```

The invention claimed is:

1. A genetically edited porcine animal comprising a genetic modification which alters the expression or activity of CD 163, wherein the genetic modification consists essentially of a deletion of exon 7 of the CD163 gene without replacing at least a portion of exon 7 of the CD163 gene.

2. A genetically edited porcine animal according to claim 1 wherein the CD163 gene has been altered to abrogate the ability of CD163 to bind to porcine reproductive and respiratory syndrome virus (PRRSV).

3. A genetically edited porcine animal according to claim 1 wherein alterations to the CD163 gene are only present in the region encoding domain 5 or flanking non-coding regions.

4. A genetically edited porcine animal according to claim 1 which is a pig which has improved tolerance to PRRSV infection.

5. A method of producing a genetically edited porcine animal comprising the steps of:
   providing a porcine animal cell;
   editing the genetic content of the cell to create a modification which alters the expression or activity of CD163, wherein the modification comprises consists essentially of a deletion of exon 7 of the CD163 gene without replacing at least a portion of exon 7 of the CD163 gene; and
   generating an animal from said cell.

6. A method according to claim 5 wherein the modification alters the region of the CD163 gene which codes for domain 5 of CD163 or flanking intronic regions.

7. A method according to claim 5 which comprises:
   introducing a site specific nuclease to the cell, the nuclease being adapted to bind to a suitable target sequence in the CD163 gene;
   incubating said cell under suitable conditions for said nuclease to act upon the DNA at or near to said target sequence; and
   thereby induce recombination, homology-directed repair or non-homologous end joining at or near the target site.

8. A method according to claim 5 which is performed on a zygote.

9. A method according to claim 5 where in the method comprises the steps of:
   providing a zygote of the porcine animal;
   introducing a site specific nuclease to the zygote which is adapted to bind to a suitable target sequence in the CD163 gene;
   incubating said zygote under suitable conditions for said nuclease to act upon the DNA at or near to said target sequence; and
   generating an animal from said genetically edited zygote.

10. A method according to claim 7 wherein the site specific nuclease comprises:
   at least one pair of transcription activator-like effector nucleases, zinc finger nucleases, or nickases;
   at least one recombinase; or
   at least one RNA-guided site-specific nuclease.

* * * * *